US006486384B1

(12) United States Patent
Zhang et al.

(10) Patent No.: US 6,486,384 B1
(45) Date of Patent: *Nov. 26, 2002

(54) METHODS AND COMPOSITIONS FOR TRANSFORMATION OF CEREALS USING CULTURED SHOOT MERISTEMATIC TISSUE

(75) Inventors: Shibo Zhang, Albany, CA (US); Myeong-Je Cho, Alameda, CA (US); Phillip Bregitzer, American Falls, ID (US); Peggy G. Lemaux, Moraga, CA (US)

(73) Assignees: The Regents of the University of California, Oakland, CA (US); The United States of America as represented by the Secretary of Agriculture, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/159,317

(22) Filed: Sep. 23, 1998

Related U.S. Application Data

(60) Provisional application No. 60/059,873, filed on Sep. 24, 1997.

(51) Int. Cl.[7] .............................. A01H 5/00; C12N 5/04; C12N 15/82; C12N 15/87
(52) U.S. Cl. ..................... 800/293; 800/320; 800/320.2; 435/470; 435/419; 435/430
(58) Field of Search ................................. 800/293, 278, 800/300.1, 320, 300, 301, 302, 320.2; 435/172.3, 424, 430, 470, 419

(56) References Cited

U.S. PATENT DOCUMENTS

| | | | |
|---|---|---|---|
| 4,699,644 A | 10/1987 | Brandt et al. | 71/27 |
| 5,164,310 A | * 11/1992 | Smith et al. | 435/172.3 |
| 5,281,529 A | 1/1994 | Zhong et al. | 435/240.45 |
| 5,320,961 A | 6/1994 | Zhong et al. | 435/240.45 |
| 5,350,688 A | 9/1994 | Matsuno et al. | 435/240.5 |
| 5,403,736 A | 4/1995 | Tanimoto | 435/240.45 |
| 5,565,355 A | 10/1996 | Smith | 435/240.49 |
| 5,589,617 A | 12/1996 | Nehra et al. | 800/205 |
| 5,610,042 A | 3/1997 | Chang et al. | 435/172.3 |
| 5,639,949 A | * 6/1997 | Lignon et al. | 800/301 |
| 5,641,664 A | 6/1997 | D'Halluin et al. | 435/172.3 |
| 5,736,369 A | 4/1998 | Bowen et al. | |
| 5,948,956 A | * 9/1999 | Lee et al. | 800/320 |
| 6,140,555 A | * 10/2000 | Reichert et al. | 800/293 |

FOREIGN PATENT DOCUMENTS

| | | | | |
|---|---|---|---|---|
| JP | 01027466 | 1/1989 | | C12N/5/00 |
| JP | 1027466 | 1/1989 | | A01H/4/00 |
| JP | 07213183 | 8/1995 | | C12N/5/00 |
| JP | 07255304 | 10/1995 | | A01H/4/00 |
| WO | WO 92/20809 | 11/1992 | | C12N/15/89 |
| WO | WO 94/13822 | 6/1994 | | C12N/15/82 |
| WO | WO 96/04392 | 2/1996 | | C12N/15/82 |

OTHER PUBLICATIONS

Bregitzer et al. Plant Cell Reports 17:941–945, 1998.*
Casas et al. In Vitro Cell. Dev. Biol.—Plant 33:92–100, 1997.*
Dahleen. Plant Cell Tissue and Organ Culture. 43:267–269, 1995.*
Gordon–Kamm et al. Plant Cell 2:603–618, 1990.*
Zhang et al. J. Plant Physiol. 148:667–671, 1996.*
Zhong et al. Planta. 187:483–489, 1992.*
Zhong et al. Plant Physiol. 110:1097–1107, 1996.*
Dahleen. Plant Cell, Tissue, and Organ Culture, vol. 43, 267–269, 1995.*
Vain et al, Osmotic treatment enhances particle bombardment–mediated treatment and stable transformation of maize, Plant Cell Reports, 1993 vol./No. 12, pp. 84–88.*
Purnhauser, (1991), "Stimulation of Shoot and Root Regeneration in Wheat Triticum Aestivum Callus Cultures by Copper," *Cereal Research Communications*, 19:419–423, Database Caba AN—93:6063.
Jain et al. (1995), "An improved procedure for plant regeneration from indica and japonica reice protoplast," *Plant Cell Reports*, 14:515–519, Database Caba AN—95:129270.
Holm et al. (1994), "Regeneration of fertile barely plants form mechanically isolated protoplasts of the fertilized egg cell," *Plant Cell*, 6:531–543, Database Caba AN—9490570.
Baillie et al., (1992), "Field evaluation of barley (*Hordeum vulgare*L.) genotypes derived from tissue culture," *Can. J. Plant Sci.*, 72:725–733.
Bhaskaran et al. (1990), "Regeneration in Cereal Tissue Culture: A Review," *Crop Science*, 30:1328–1337.
Bregitzer, (1992), "Plant Regeneration and Callus Type in Barley: Effects of Genotype and Culture Medium," *Crop Science*, 32:1108–1112.
Bregitzer et al., (1995), "Plant regeneration from barley callus: Effects of 2,4–dichlorophenoxyacetic acid and phenylacetic acid," *Plant Cell*, 43:229–235.
Christensen et al., (1996), "Ubiquitin promoter–based vectors for high–level expression of selectable and/or screenable marker genes in monocotyledonous plants," *Transgenic Research*, 5:1–6.

(List continued on next page.)

Primary Examiner—David T. Fox
Assistant Examiner—David H Kruse
(74) Attorney, Agent, or Firm—Morrison & Foerster LLP

(57) ABSTRACT

Methods for transforming plants, particularly commercial genotypes of cereals, are provided. The methods involve transformation of meristematic organogenic tissue, and include the use of defined plant growth media. The methods disclosed provide more stable transgenic plants, and permit the transformation of varieties of cereals that are not amenable to transformation by conventional approaches.

7 Claims, No Drawings

OTHER PUBLICATIONS

Dahleen, (1995), "Improved plant regeneration from barley callus cultures by increased copper levels," *Plant Cell*, 43:267–269.

De Block et al., (1987), "Engineering herbicide resistance in plants by expression of detoxifying enzyme," *The EMBO Journal*, 6(9):2513–2518.

Fletcher, (1969), "Retardation of Leaf Senescence by Benzyladenine in Intact Bean Plants," *Planta*, 89:1–8.

Fromm et al., (1986), "Stable transformation of maize after gene transfer by electroporation," *Nature*, 319:791–793.

Fromm et al., (1989), "An Octopine Synthase Enhancer Element Direct Tissue–Specific Expression and Binds ASF–1, a Factor from Tobacco Nuclear Extracts," 1:977–984.

Funatsuki et al., (1995), Fertile transgenic barley generated by direct DNA transfer to protoplasts, *Theor. Appl. Genet.*, 91:707–712.

Ghaemi et al., (1994), "The effects of silver nitriate, colchicine, cupric sulfate and genotype on the production of embryoids from anthers of tetraploid wheat (*Triticum turgidum*)," *Plant Cell*, 36:355–359.

Gless et al., (1998), Transgenic Oat Plants Obtained at High Efficiency by Microprojectile Bombardment of Leaf Base Segments, *J. Plant Physiol*, 152:151–157.

Goldstein et al., (1986), issue culture and plant regeneration from immature embryo explants of Barley, *Hordeum vulgare*, *Theor. Appl. Genet.*, 71:631–636.

Gordon–Kamm et al., (1990), "Transformation of Maized Cells and Regeneration of Fertile Transgenic Plants," *The Plant Cell*, 2:603–618.

Griffin et al., (1995), "High–frequency plant regeneration from seed–derived callus cultures of Kentucky bluegrass (*Poa pratensis* L.)," *Plant Cell Reports*, 14:721–724.

Hagio et al., (1995), "Production of fertile transgenic barley (*Hordeum vulgare* L.) plant using the hygromycin–resistance marker," *Plant Cell Reports*, 14:329–334.

Hanzel et al., (1985), "Genotype and Media Effects on Callus Formation and Regeneration in Barley," *Crop Science*, 25:27–31.

Holtorf et al., (1995), "Two routes of chlorophyllide synthesis that are differentially regulated by light in barley (*Hordeum vulgare* L.)," *Proc. Natl. Acad. Sci. USA*, 92:3254–325.

Jähne et al., (1991), "Regeneration of fertile plants from protoplasts derived from embryogenic cell suspensions of barley (*Hordeum vulgare* L.)," *Plant Cell Reports*, 10:1–6.

Jähne et al., (1994), "Regeneration of transgenic, microspore–derived, fertile barley," *Theor. Appl. Genet.*, 89:525–533.

Kasha et al., (1990), "Haploids In General Improvements: Anther and Microspore Culture," *Gene Manipulation in Plant Improvements II*, In: Gene Manipulation in Plant Improvement II, Gustafson (ed)., Premier Press, New York, pp. 213–235.

Kott et al., (1984), "Initiation and morphological development of somatic embryoids from barley cell cultures," *Can. J. Bot.*, 62:1245–1249.

Lemaux et al., (1996), "Bombardment–Mediated Transformation Methods for Barley," *Bio–Rad*, US/EG Bulletin 2007:1–6.

Lührs et al., (1987), "Plant regeneration in vitro from embryogenic cultures of spring– and winter–type barley (*Hordeum vulgare* L.) varieties," *Theor. Appl. Genet.*, 75:16–25.

Murakami et al., (1986), "The bialaphos biosynthetic genes of *Streptomyces hygroscopicus*: Molecular cloning and characterization of the gene cluster," *Mol. Gen. Genet.*, 205:42–50.

Napoli et al., (1990), "Introduction of a Chimeric Chalcone Synthase Gene into Petunia Results in Reversible Co–Suppression of Homologous Genes in trans," *The Plant Cell*, 2:279–289.

Potrykus (1991), "Gene Transfer to Plants: Assessment of Published Approaches and Results," *Annu. Rev. Plant Physiol. Plant Mol. Biol.*, 42:205–225.

Salmenkallio–Marttila et al. (1995), "Transgenic barley (*Hordeum vulgare* L.) by electroporation of protoplasts," *Plant Cell Reports*, 15:301–304.

Somers et al. (1992), "Fertile, Transgenic Oat Plants," *Biotechnology*, 10:1589–1594.

Thompson et al. (1987), "Characterization of the herbicide–resistance gene bar from *Streptomyces hygroscopicus*," *The EMBO Journal*, 6(9):2519–2523.

Torbert et al. (1995), "Use of paromomycin as a selective agent for oat transformation," *Plant Cell Reports*, 14:635–640.

Wan & Lemaux (1994), "Generation of Large Numbers of Independently Transformed Fertile Barley Plants," *Plant Physiol.*, 104:37–48.

Wan & Lemaux (1994), "Biolistic Transformation of Microspore–Derived and Immature Zygotic Embryos and Regeneration of Fertile Transgenic Barley Plants," In: Gene Transfer to Plants, eds. Potrykus and Spangenberg, Springer Verlag, pp. 139–146.

Wan et al. (1995), "Type I callus as a bombardment target for generating fertile transgenic maize (*Zea mays* L.)," *Planta*, 196:7–14.

Zaghmout & Torello (1992), "Plant Regeneration from Callus and Protoplasts of Perennial Ryegrass (*Lolium perenne* L.)," *J. Plant Physiol.*, 140:101–105.

Zhang et al. (1996), Production of Multiple Shoot Apical Meristems of Oat (*Avena sativa* L.), *J. Plant Physiol.*, 148:667–671.

Zhong et al. (1991), "Plant regeneration via somatic embryogenesis in creeping bentgrass (*Agrostis palustris* Huds.)," *Plant Cell Reports*, 10:453–456.

Zhong et al. (1992), "In–vitro morphogenesis of corn (*Zea mays* L.)," *Planta*, 187:483–489.

Zhong et al. (1996), "The Competence of Maize Shoot Meristems for Integrative Transformation and Inherited Expression of Transgenes," *Plant Physiol.*, 110:1097–1107.

\* cited by examiner

METHODS AND COMPOSITIONS FOR TRANSFORMATION OF CEREALS USING CULTURED SHOOT MERISTEMATIC TISSUE

PRIORITY CLAIM

This application claims priority from co-pending U.S. provisional application Ser. No. 60/059,873, filed Sep. 24, 1997, which is herein incorporated by reference.

STATEMENT OF GOVERNMENT RIGHTS

This invention was made with U.S. Government support under the Specific Cooperative Agreement No. 5366-21000-014114S awarded by he USDA/ARS. The Government has certain rights in this invention.

BACKGROUND OF THE INVENTION

This invention relates to compositions and methods for the in vitro culture, transformation, and regeneration of plants.

Genetic improvement of various crop species by genetic engineering has sometimes been hindered because techniques for in vitro culture, transformation, and regeneration of amenable cultivars are less effective with recalcitrant commercial cultivars.

The ability to genetically engineer monocots, including cereal crops, to improve their performance and pest-resistance or to enhance alternative uses is of great importance. The practical utility of stable transformation technologies is largely dependent on the availability of efficient methods for generating large numbers of fertile green plants from tissue culture materials.

Virtually all current genetic engineering technologies require that genes be delivered to cells grown in vitro. Most published methods for generating fertile transformed plants from cereals (e.g. rice, wheat, maize, oat, sorghum, triticale, barley and rye) utilize as initial explants the immature scutellum of the embryo or microspores directly or tissue derived from immature embryos or microspores. From these initial explants, cellular proliferation occurs. After selection or screening for transformants, plants are regenerated.

Five critical problems adversely impact the utility of these transformation methods, particularly monocot species such as cereals and grasses. The first is heritable variability, termed "somaclonal variation" which results from spontaneous and heritable genetic changes in cultured plant tissues. Somaclonal variation can adversely affect the field performance (e.g., height, yield, and seed weight) of tissue culture-derived plants. Somaclonal variation can also limit the use of transgenic plants for breeding, since introgression of transgenes from such plants into acceptable genetic backgrounds can require multiple cycles of hybridization and progeny analysis, particularly if one or more heritable mutations were closely linked to the transgene or to genes controlling other critical traits.

The second problem is related to the increase in the incidence of albino plants caused by, for example, the physiological and biochemical changes imposed by selection, by the increased time frame required for selection during transformation and/or with changes in genotype. With some genotypes published methods of transformation result in the selection of transformed callus that is either nonregenerable or regenerates albino plants.

The third problem is the genotype dependence of the in vitro culture response of various explants, e.g. scutellum- and microspore-derived tissues and the resulting difficulties in applying transformation methods developed for amenable genotypes to commercially important more recalcitrant genotypes.

The fourth problem is related to the instability of the introduced genes themselves or of the expression of the transgenes. In transgenic cereals the introduced gene is sometimes lost in subsequent generations and there can also be a loss of the ability of the plant to express a transgene.

The fifth problem is that transgenic plants produced by published methods are often polyploid and therefore cannot be propagated as the more desirable diploid varieties, further limiting the usefulness of transgenic plants in breeding programs.

Aspects of the in vitro culturing and/or transformation process are likely to be responsible for or related to these and other problems encountered in efforts to genetically engineer plant species, including monocots such as cereals and grasses. Most transformation protocols require that the target tissue undergo embryogenesis, which may include de-differentiation of a single original transformed cell before the sustained cell divisions that give rise to an embryo consisting mostly or entirely of cells that contain the introduced DNA. De-differentiation during in vitro culturing introduces stresses on the genome, causing modifications of the genome that are associated with somaclonal variation, including DNA methylation, point mutations, deletions, insertions, and the generation of gross cytogenetic abnormalities. These genomic modifications lead to subsequent phenotypic abnormalities and performance losses and may contribute to the other problems listed above.

Transformation methods using excised shoot apices have been previously described (see, for example, U.S. Pat. No. 5,164,310 to Smith et al.; Zhong et al., 1996). However, these methods have not proven to be effective for some monocots, including commercially important varieties of barley, oat and wheat. For example, until now there is no method known for transformation of the spring barley cultivar (Hordeum vulgare L.) Harrington, which is a widely grown two-rowed malting barley.

There is a need, therefore, for improved methods for plant transformation and regeneration, particularly for use with monocot species such as cereals and grasses.

SUMMARY OF THE INVENTION

The invention provides methods and compositions for plant transformation and regeneration that are applicable to a wide variety of monocots, including commercially important cereal genotypes that have proven difficult or impossible to transform and regenerate by previously available methods. These improved methods result in significantly higher regeneration frequencies, reduced somaclonal variation, improved transgene expression stability, and reduced albinism.

The invention is based on the discovery that transgenic plants produced by transformation of organogenic tissues, particularly tissues derived from shoot meristematic cells, are generally healthier than plants produced by conventional transformation of embryogenic tissues. In particular, transgenic plants produced by transformation methods provided by the invention may be more stable, exhibit fewer problems associated with methylation, show fewer mutations caused by somaclonal variation, and exhibit reduced albinism. In addition, the transformation methods disclosed are applicable to commercial varieties of monocots such as barley, wheat and oat that are recalcitrant to conventional transformation methods.

The transformation method disclosed relies on introducing the nucleic acid sequence (generally referred to as the "transgene") into shoot meristematic tissue that is typically derived from a shoot apex or a leaf base. This tissue requires little or no de-differentiation in order to regenerate plants that express the transgene. Thus, in contrast to embryogenic callus tissue (a conventional target for transformation), these meristematic tissues do not undergo significant de-differentiation in the transformation process. Rather, these cells require only a simple redirection of growth in order to produce whole transgenic plants. The present invention also provides plant growth media containing growth substrates (including suitable levels of plant hormones and other components) with which the efficient production and regeneration of this meristematic tissue can be achieved. In particular, the invention provides media suitable for the production of meristematic tissue that is highly amenable to transformation from cultivars of monocots that are otherwise recalcitrant to transformation.

In general terms, the transformation method provided by the invention comprises obtaining shoot meristematic tissue from the plant to be transformed. Any source of shoot meristematic tissue may be employed, including shoot meristematic tissue taken from shoot apices of embryos and seedlings or axillary or adventitious shoots.

The meristematic tissue is incubated in the light on a meristem proliferation medium (MPM) to induce production of adventitious meristematic cells, which are then used as the target for nucleic acid transformation. Transformation may be achieved by any effective means, including for example conventional particle bombardment. MPM promotes fast growth of meristematic cells without promoting shoot or root formation. Particular compositions of MPM that are provided by this invention include components such as maltose and copper that are important to the success of the transformation methods; these compositions are designated as MPM-MC. MPM-MC typically comprises plant auxin and cytokinin hormones, usually in a low auxin/high cytokinin ratio. Thus, MPM-MC typically includes from 0 mg/l to about 3 mg/L of an auxin and from about 1 mg/L to about 10 mg/l of a cytokinin. MPM-MC also includes an elevated level of copper, generally from about 0.1 $\mu$M to about 50 $\mu$M, and typically within the range of about 1 to about 10 $\mu$M. In addition, maltose is generally used as a carbon/sugar source in MPM-MC medium, typically at a concentration of from about 20 g/L to about 60 g/L, and usually at about 30 g/L. Other carbon sources, such as sucrose, may be used in place of, or in combination with, maltose. The invention provides particular combinations of these MPM-MC components that are especially suitable for use in transforming monocot species that were previously not amenable to transformation.

Following introduction of the nucleic acid, the meristematic tissues are typically transferred to fresh MPM-MC and incubated in the light. Thereafter, a selection agent may be introduced to the culture medium in order to select for transformed meristematic cells and meristematic structures. Transformed cells and structures are identified by their enhanced growth on this selection medium compared to untransformed material, and are subsequently removed and transferred to a regeneration medium for rooting.

The disclosed methods may be used not only for wheat, barley and oat, but also for other monocots, such as rice, maize, sorghum, millet, rye, triticale, forage grass and turfgrass.

These and other aspects of the invention will become more apparent from the following detailed description.

DETAILED DESCRIPTION OF THE INVENTION

I. Shoot Meristematic Tissue as a Target Tissue for Plant Transformation

The transformation method of the present invention is based on the introduction of nucleic acids into meristematic tissues derived from any suitable source including, but not limited to, shoot meristems and leaf base tissue. These cells appear to require only a simple redirection of cells in the tissues for the formation of shoots and plants to occur in culture, unlike cells derived from an immature embryo or microspore which require an apparent de-differentiation process. The determination that a particular tissue observed in culture is meristematic shoot tissue (rather than embryogenic tissue) may be made based on a molecular analysis of the expression of certain genes which, as described in section II and Example 1 below, are shown to be expressed primarily in meristematic tissue and not in embryogenic tissue. This molecular approach permits the scientists subjective visual determination of meristematic tissues to be verified objectively.

Following introduction of the nucleic acids into the target meristematic cells, incubation without selection permits the meristematic tissue to proliferate, and allows the transformed tissue to become established. Subsequent application of a selection agent permits the transformed tissue to be selected. After the tissue has been selected (generally through multiple transfers to fresh selection medium to insure that the tissue comprising the meristematic domes is uniformly transformed), plants are induced to develop by removing or reducing the levels of hormones (particularly auxins) in the culturing medium (i.e., transfer to regeneration medium, RM). Plants can also be induced earlier in the selection process and resulting plants can be screened for presence of a transgene in the germline, thereby reducing the amount of time the tissue is cultured.

The use of meristematic tissue has several advantages for transformation. In particular, the adverse effects of a callus phase are eliminated, possibly because de-differentiation of the tissue does not occur (or occurs to a lesser extent) than during callus formation. Rather, adventitious meristems likely arise from a simple redirection of cells in the meristem or leaf base and not from de-differentiation.

Methylation problems associated with transformation of embryogenic tissue are reduced. An examination of barley plants arising from tissue that was derived from either immature embryos or meristems showed those derived from in vitro cultured meristems have fewer methylation changes at the genomic level and exhibit less somaclonal variation than plants derived from embryogenic callus. In addition, no albino plants were produced from meristem cultures, even after subculturing in vitro for more than one year. There is typically also less polyploidy in the meristem-derived regenerated plants and improved transgene expression stability.

In addition, the methods of the present invention are effective with a wider variety of genotypes than other transformation techniques, since de-differentiation of plant tissues, which is more genotype-dependent, is not required.

The methods of the present invention do not require the work- and resource-intensive maintenance of plants grown under controlled growth conditions as donor material that is required for many other transformation methods. This is because meristematic tissue can be derived from the developing shoot apices obtained by germinating dry seeds. By the methods of the present invention, meristematic cells derived from vegetative shoot meristems or young leaf bases can be proliferated in vitro and manipulated to give rise to plants through direct organogenesis (vegetative shoot meristem formation), eliminating the need to maintain the tissue in a de-differentiated state, and thereby reducing genomic instability. In addition proliferating meristematic tissue can be maintained for long periods without reduction in regenerative capacity.

The methods of the present invention are applicable to any plant species, including both dicot and monocot species, including, but not limited to barley, oat, wheat, rice, rye, triticale and turf and forage grasses. The disclosed methods are particularly useful for transformation of commercial varieties of wheat, barley and oat (e.g., barley genotypes Harrington, Morex, Galena, Steptoe, Moravian II, wheat genotypes Yecora Rojo, Bobwhite, Karl and Anza and oat genotypes Garry Gerry, Prone, Porter, Pacer and Ogle) that are recalcitrant to transformation using published embryogenic callus approaches.

II. Molecular Markers for Direct Organogenesis or Shoot Meristem Formation from In Vitro Cultured Tissue Many plant somatic cells are totipotent and typically undergo in vitro regeneration via adventitious shoot meristem formation/development or somatic embryo formation. Adventitious shoot meristem formation/development, or organogenesis, is the process by which totipotent cells or tissues produce a unipolar structure, the shoot or root (including a shoot or root meristem, respectively), the vascular system of which is often connected to the parent tissue. Organogenesis likely results from a switch in the developmental program of pre-existing meristematic cells. In contrast, somatic embryogenesis occurs when a bipolar structure containing a root and shoot axis with a closed independent vascular system is produced from certain cells in the scutellum of the immature embryo or with cultured microspores. Somatic embryogenesis likely results from de-differentiation followed by a re-engagement of the whole developmental process in which plant cells participate during normal development of the zygotic embryo. A single isolated cell is able to develop normally into a whole plant via either formation of shoot meristem or somatic embryo, suggesting that the developmental program for formation of a shoot meristem or somatic embryo is contained within the cell.

In order to distinguish between embryogenic and organogenic tissue in culture, it has been necessary to rely on histology or on gross morphological features that are difficult to distinguish. The present invention identifies molecular markers that can be used to distinguish embryogenic from organogenic tissues far more easily and reliably, e.g., using immunological, molecular or microscopy methods. Thus, it is shown that expression of the knotted gene (e.g., maize kn1), for example, can be used to distinguish a shoot meristem from an embryo and to characterize shoot meristem proliferation in oat, barley, orchard grass and maize. Using anti-KN1 antibodies to assess KN1 expression during adventitious shoot meristem formation in in vitro-proliferating axillary shoot meristems of maize, barley and oat, it is shown that adventitious shoot meristems appear to arise directly from meristematic cells in the enlarged meristematic domes formed during in vitro culturing that express KN1 or KN1 homolog(s). These results provide molecular evidence that the in vitro morphogenic route in the described culture system is organogenesis.

Molecular markers for meristematic cells such as expression of KN1 and cdc2Zm permit one to identify meristematic tissues that can be used as target tissues for transformation. These molecular markers can also be used to assess whether modifications to a plant cell culture protocol such as the protocols provided herein promotes organogenesis and thus the ability to regenerate fertile green plants from cells cultured using the modified protocol.

III. Plant Culture Media and Methods

Unless otherwise noted, terms are to be understood according to conventional usage by those of ordinary skill in the relevant art. In addition to the definitions of terms provided below, definitions of common terms in molecular biology may also be found in Rieger et al., 1991; and Lewin, 1994.

a. In Vitro Culture of Meristematic Transformed Plant Cells

Meristematic tissue is comprised of undifferentiated plant cells that are capable of repeated division to yield other meristematic cells as well as differentiated cells that elongate and further specialize to form structural tissues and organs of the plant. Mersitematic tissue for use in the transformation methods described herein may be obtained from the shoot apices of seedlings or plants, as well as leaf bases.

The media used for in vitro culture of shoot meristematic tissue to produce adventitious meristems and to regenerate transformed meristematic tissue contribute significantly to the successful production of fertile transgenic plants. In addition, selection of fast-growing tissue improves the long-term regenerability of the cultures.

b. Meristem Proliferation Medium (MPM)

Meristematic tissue isolated from a plant (e.g., shoot apices) is cultured on MPM medium, which promotes a fast growth rate and proliferation of meristematic cells without promoting shoot and root formation. In addition, following DNA introduction into meristematic tissue, the transformed tissues are incubated on MPM for a time sufficient for individual transformed cells to proliferate, thereby ensuring that a sufficient number of progeny cells are produced from each transformation event to increase the likelihood that the initial transformation event leads to the regeneration of a plant containing transformed tissue.

MPM preferably has a low auxin/high cytokinin ratio. Auxin levels in MPM are typically about 0 mg/L (no auxin) to about 3.0 mg/L. For barley and wheat, for example, the preferred levels are about 0 mg/L to about 0.5 mg/L. For oat, no auxin is needed for optimal results. Cytokinin levels in MPM are typically about 1 mg/L to about 10 mg/L. For barley, wheat and oat, for example, about 2 mg/L to about 4 mg/L are preferred. Cytokinins may improve regenerability and reduce the incidence of albinism. The optimal level of cytokinin (and particularly the optimal ratio of auxin to cytokinin) depends on the genotype and the species being transformed.

Any well-known auxin or cytokinin may be used in MPM or regeneration medium (RM). Auxins include, but are not limited to, dichlorophenoxyacetic acid [2,4-D], dicamba, indoleacetic acid, picloran and naphthalenacetic acid. 2,4-D is preferred for barley, wheat and oat. Cytokinins include, but are not limited to, 6-benzylaminopurine [BAP], kinetin, zeatin, zeatin riboside, and $N^6$-(2-isopentenyl)adenine (2iP). BAP and 2iP are typically employed for barley transformation, particularly BAP. A particular genotype or species may respond optimally to a specific phytohormone.

MPM-MC refers to the particular formulation of MPM used in certain aspects of the invention. MPM-MC is formulated with hormones as described above, and is supplemented with maltose and copper. MCM-MC contains copper generally at a concentration of at least 0.1 $\mu$M (the level in typical plant growth media, such as MS medium), and more typically at least 10–100 fold higher, i.e. from about 1 to about 10 μM. In certain formulations, MPM contains even higher levels of copper, for example up to about 50 μM. Optimal copper levels vary with the genotype and species. The term "copper" is intended to include any well-known nutritional source of copper for plant culture media, e.g., cupric sulfate.

In addition, MPM also includes a sugar/carbon source, generally at about 20 g/L to about 60 g/L, with about 30 g/L being typical. In MPM-MC maltose is the preferred carbon/sugar source, particularly for recalcitrant barley and wheat genotypes such as Harrington (barley) and Anza and Yecora Rojo (wheat) although sucrose or other conventional carbon sources for plant tissue culture can also be used (e.g., with barley genotype Golden Promise and oat).

Maltose and elevated copper levels were tested separately and in combination in various formulations of MPM to observe their effects on in vitro culture of adventitious meristems. In some barley and wheat genotypes, the combination of maltose and elevated copper levels was critical for the successful long-term proliferation of shoot meristematic tissue and dramatically improved the shoot meristem proliferation efficiency in Harrington (in which 80–90% of meristems cultured gave rise to proliferating adventitious meristematic tissue), in Crystal (50–70%), and in Morex (30–40%). Without the combination of maltose and elevated copper levels, none of the barley meristems gave rise to long-term cultures. Maltose alone reduced the production of brownish tissue, which had a negative effect on in vitro growth of the meristems, and elevated copper alone promoted plant development. However, the combination of maltose and copper was necessary to produce long-term regenerable meristematic tissues. In addition selection of fast-growing tissue was also important for obtaining long-term regenerative cultures.

As discussed in the Examples below, optionally MPM can be supplemented with a conventional osmoticum for a short time (e.g., about 4 hours) prior to (and, optionally, for a short period after) microprojectile bombardment. For example, the MPM can be supplemented with equimolar mannitol and sorbitol to give a final concentration of 0.4 M. However, good results have also been obtained when such an osmoticum was not included in MPM prior to (or after) bombardment.

As noted above, the methods and media described herein can be used to produce and maintain adventitious meristematic tissue for long periods of time. To maintain adventitious meristematic tissue, it is generally divided into smaller pieces (e.g., pieces of about 3 to 5 mm for barley) and subcultured, i.e., transferred to fresh medium, at regular intervals to promote optimal growth rates.

If a selectable marker is used to select for transformed tissues, the meristematic tissues may be initially cultured after transformation without selection in order to allow for the proliferation of transformed cells in the absence of dead or dying cells resulting from the selection agent. The optimal period for proliferation without selection varies with the species. After this period, selection can be applied to select for transformed cells. Selection can be accomplished by adding a selection agent to the culture medium for which the foreign DNA in transformed cells confers resistance (assuming that a selectable marker is included on the foreign DNA). Putative transformants are identified by their faster growth on the selective medium relative to nontransformed tissue. Screenable markers (e.g., green fluorescent protein and β-glucuronidase) can also be used to identify transformed tissue.

Transformed tissues are generally maintained under light (for barley and wheat, approximately 10–30 μEinsteins). The use of light reduces or eliminates the regeneration of albino plants and improves regenerability.

As used herein, "plant culture medium" refers to any medium used in the art for supporting viability and growth of a plant cell or tissue, or for growth of whole plant specimens. Such media commonly include defined components including, but not limited to: macronutrient compounds providing nutritional sources of nitrogen, phosphorus, potassium, sulfur, calcium, magnesium, and iron; micronutrients, such as boron, molybdenum, manganese, cobalt, zinc, copper, chlorine, and iodine; carbohydrates (preferably maltose for barley, although sucrose may be better for some species); vitamins; phytohormones; selection agents (for transformed cells or tissues, e.g., antibiotics or herbicides); and gelling agents (e.g., agar, Bactoagar, agarose, Phytagel, Gelrite, etc.); and may include undefined components, including, but not limited to: coconut milk, casein hydrolysate, yeast extract, and activated charcoal. The medium may be either solid or liquid, although solid medium is preferred.

Any conventional plant culture medium can be used as a basis for the formulation of MPM and RM when appropriately supplemented as described herein. In addition to the plant culture media discussed in the Examples below (e.g., MS medium and FHG medium), a number of such basal plant culture media are commercially available from Sigma (St. Louis, Mo.) and other vendors in a dry (powdered) form for reconstitution with water.

c. Regeneration Medium.

"Regeneration medium" (RM) promotes differentiation of totipotent plant tissues into shoots, roots, and other organized structures and eventually into plantlets that can be transferred to soil. Auxin levels in regeneration medium are reduced relative to MPM or, preferably, auxins are eliminated. It is also preferable that copper levels are reduced (e.g., to levels common in basal plant culture media such as MS medium). It is preferable to include a cytokinin in RM, as cytokinins have been found to promote regenerability of the transformed tissue. However, regeneration can occur without a cytokinin in the medium. Typically, cytokinin levels in RM are from about 0 mg/L to about 4 mg/L. For barley and wheat, about 2 mg/L of a cytokinin is preferred, and the preferred cytokinin is BAP. RM also preferably includes a carbon source, preferably about 20 g/L to about 30 g/L, e.g., either sucrose or maltose (there is no preference for maltose for RM).

Optionally, one may employ a conventional shooting medium to promote shoot regeneration from meristematic structures and/or a conventional rooting medium to promote root formation. For example, MS basal medium supplemented with IBA (e.g., 0.5 mg/L) can be used to induce root formation, if necessary. Root induction is preferred for corn but appears to generally be unnecessary with oat and barley. Depending upon the genotype, different levels of an auxin and cytokinin (i.e., a different auxin/cytokinin ratio) provide optimal results. Conventional shooting and rooting media are considered regeneration media.

Any well-known regeneration medium may be used for the practice of the methods of the present invention. For barley, FHG medium (Hunter, 1988, and described in Kasha et al., 1990) can be used, for example.

d. Introduction of Nucleic Acids

A number of methods can be used to introduce nucleic acids into the meristematic cells, including particle bomardment. Particle bombardment has been employed for transformation of a number of plant species, including barley (see, e.g., Wan and Lemaux, 1994, and BioRad Technical Bulletin 2007) and corn (see, e.g., Gordon-Kamm et al., 1990, Wan et al., 1995), for example. Successful transformation by particle bombardment requires that the target cells are actively dividing, accessible to microprojectiles, culturable in vitro, and totipotent, i.e., capable of regeneration to produce mature fertile plants. As described herein, a meristematic tissue (including, but not limited to a vegetative shoot meristem, such as an apical meristem from primary or axillary shoots, or a young leaf base) is cultured in vitro to caused to formation of adventitious meristems, and the adventitious meristem cells are the target for bombardment.

Microprojectile bombardment can be accomplished at normal rupture pressures, e.g., at about 1100 psi, although lower rupture pressures can be used to reduce damage of the target tissue, e.g., about 600 to 900 psi. It has been found that meristematic tissues recover better from the tissue damage caused by bombardment than callus tissue, permitting higher rupture pressures to be used.

In addition to particle bombardment, conventional methods for plant cell transformation may be used, including but not limited to: (1) Agrobacterium-mediated transformation, (2) microinjection, (3) polyethylene glycol (PEG) procedures, (4) liposome-mediated DNA uptake, (5) electroporation, and (6) vortexing with silica fibers.

e. Definitions and Explanations of Terms Used

The following definitions and explanations are provided to facilitate understanding of the invention.

Plant: The term "plant" encompasses transformed plants, progeny of such transformed plants, and parts of plants, including reproductive units of a plant, fruit, flowers, seeds, etc. The transformation methods and compositions of the present invention, are particularly useful for transformation of cereal genotypes that are recalcitrant to other transformation methods. Such cereals include barley (e.g., genotypes Morex, Harrington, Crystal, Stander, Moravian III, Galena, Salome, Steptoe, Klages and Baronesse), wheat (e.g., genotypes Yecora Rojo, Bobwhite, Karl and Anza) and oat (e.g., genotypes Garry Gerry, Prone, Porter, Pacer and Ogle). Other species of monocotyledonous and dicotyledonous plants may also be transformed using the disclosed methods.

Reproductive unit: A reproductive unit of a plant is any totipotent part or tissue of the plant from which one can obtain progeny of the plant, including, for example, seeds, cuttings, tubers, buds, bulbs, somatic embryos, microspores, cultured cells (e.g., callus or suspension cultures), etc.

Isolated: An isolated nucleic acid is one that has been substantially separated or purified away from other nucleic acid sequences in the cell of the organism in which the nucleic acid naturally occurs, i.e., other chromosomal and extrachromosomal DNA and RNA. The term also embraces recombinant nucleic acids and chemically synthesized nucleic acids.

Operably Linked: Nucleic acids can be expressed in plants or plant cells under the control of an operably linked promoter that is capable of driving expression in a cell of a particular plant. A first nucleic-acid sequence is operably linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary, to join two protein coding regions to produce a hybrid protein.

Recombinant: A recombinant nucleic acid is made by an artificial combination of two otherwise separated segments of sequence, e.g., by chemical synthesis or by the manipulation of isolated segments of nucleic acids by conventional genetic engineering techniques.

Transformed; Transgenic: A cell, tissue, organ, or organism into which a foreign nucleic acid, such as a recombinant vector, has been introduced is considered "transformed" or "transgenic," as is progeny thereof in which the foreign nucleic acid is present. A transformed tissue or plant may include some cells that are not transformed, i.e., may be chimaeric, comprising transformed and untransformed cells. Such chimaeric tissues may be used to regenerate transformed plants, and may be advantageous for this purpose since less in vitro propagation and selection will be required to produce chimaeric tissues than tissues in which 100% of the cells are transformed. Regeneration of chimaeric tissues will generally give rise to chimaeric plants, i.e., plants comprised of transformed and non-transformed cells. Reproduction of these chimaeric plants by asexual or sexual means may be employed to obtain plants entirely comprised of transformed cells.

"Foreign" nucleic acids are nucleic acids that would not normally be present in the host cell, particularly nucleic acids that have been modified by recombinant DNA techniques. The term "foreign" nucleic acids also includes host genes that are placed under the control of a new promoter or terminator sequence, for example, by conventional techniques.

Vectors, Transformation, Host cells: Nucleic acids can be incorporated into recombinant nucleic-acid constructs, typically DNA constructs, capable of being introduced into and replicating in a host cell. Such a construct preferably is a vector that includes sequences that are capable of transcription and translation of a polypeptide-encoding sequence in a given host cell (and may include a replication system, although direct DNA introduction methods conventionally used for monocot transformation do not require this).

For the practice of the present invention, conventional compositions and methods for preparing and using vectors and host cells are employed, as discussed, inter alia, in Sambrook et al., 1989, or Ausubel et al., 1992.

A number of vectors suitable for stable transformation of plant cells or for the establishment of transgenic plants have been described in, e.g., Pouwels et al., 1987, Weissbach and Weissbach, 1989, and Gelvin et al., 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters useful for expressing genes in plant cells include, but are not limited to, the cauliflower mosaic virus (CaMV) 35S promoter, maize ubiquitin (Ubi-1) promoter, rice actin (Act) promoter, nopaline synthase promoter, and the octopine synthase promoter. A variety of plant gene promoters that are regulated in response to environmental, hormonal, chemical, and/or developmental signals also can be used for expression of foreign genes in plant cells, including promoters regulated by heat (e.g., heat shock promoters), light (e.g., pea rbcS-3A or maize rbcS promoters or chlorophyll a/b-binding protein promoter); phytohormones, such as abscisic acid; wounding (e.g., wunI); anaerobiosis (e.g., Adh); and chemicals such as methyl jasminate, salicylic acid, or safeners. It may also be advantageous to employ well-known organ-specific promoters such as endosperm-, embryo-, root-, phloem-, or trichome-specific promoters, for example.

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Such vectors also generally include one or more dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin acetyltransferase or glyphosate) to facilitate manipulation in bacterial systems and to select for transformed plant cells.

Screenable markers are also used for plant cell transformation, including color markers such as genes encoding β-glucuronidase (gus) or anthocyanin production, or fluorescent markers such as genes encoding luciferase or green fluorescence protein (GFP).

The invention is illustrated by the following Examples.

EXAMPLES

Example 1
The Use of Molecular Markers to Objectively Identify Meristematic Tissue Genes critical to cell division and development are useful for investigating the molecular mechanisms of in vitro plant morphogenesis. cdc2 encodes a cyclin-dependent kinase (CDK p34) that plays a central role in the eukaryotic cell cycle. Recently, cdc2 homologues were isolated from plant species, such as *Arabidopsis thaliana* (Ferreira et al. 1991), *Medicago sativa* (Hirt et al. 1991), *Pisum sativum* (Feiler and Jacobs 1990), *Antirrhinum majus* (Fobert et al. 1994), and *Zea mays* (Colasanti et al. 1991). In the plant species analyzed, expression of cdc2 was observed mainly in actively proliferating cells, e.g., in shoot meristems or young leaves (Colasanti et al. 1991; Fobert et al. 1994; Martinez et al. 1992). CDC2Zm in maize root tips and stomatal complex cells was localized mainly in the nucleus at interphase and early prophase and was associated with the preprophase band (Colasanti et al. 1993). In Arabidopsis, expression of cdc2a is linked with competence for cell division (Hemerly et al. 1993). These results suggest that cdc2 is a critical gene in the regulation of plant cell division. We have found that the expression of cdc2 is a useful molecular marker for identification of dividing or division-competent cells in plant tissues.

The expression of knotted1 (kn1) is a reliable molecular marker for shoot meristem formation during zygotic embryogenesis in maize (Smith et al. 1995). In the developing maize plant, KN1 is expressed in the meristems of vegetative shoots and inflorescences, but not in leaf primordia, developing leaves or lateral floral organs (Smith et al. 1992). kn1 was first cloned from maize (Hake et al., 1989), and homologs of kn1 have been isolated from other plant species, such as *Oryza sativa* (Matsuoka et al. 1993), *Arabidopsis thaliana* (Lincoln et al. 1994; Long et al. 1996), *Lycopersicon esculentum* (Hareven et al. 1996) and *Hordeum vulgare* (Müller et al. 1995). In Arabidopsis, the expression patterns of KN1-homologs (KNAT1 and STM) were similar to those of KN1 in maize (Lincoln et al. 1994; Long et al. 1996). Ectopic expression of KN1 or a KN1-homolog is sufficient to induce shoot or inflorescence meristem formation from differentiated leaf tissues in dicotyledonous species, such as tobacco (Sinha et al. 1993) and Arabidopsis (Chuck et al. 1996). Expression of KN1 or certain KN1-homologs is a reliable molecular marker for identifying cells involved in shoot meristem formation in plants.

The expression of CDC2Zm and KN1 were studied during adventitious shoot meristem formation from in vitro proliferation of axillary shoot meristems in maize and barley. The evolutionary conservation of these two proteins allowed immunolocalization of the proteins in maize and cross-reacting protein(s) in barley. The expression of these two genes can be used as molecular markers to objectively identify meristematic tissues Materials and methods Mature seeds (the husk was removed by hand for barley) were soaked in 70% ethanol for 2–3 min, washed 3× with sterilized water, sterilized with 30% (v/v) bleach (5.25% sodium hypochlorite) for 20–30 min (depending on seed source), and rinsed again with sterilized water 3×. Sterilized seeds were germinated on MS basal medium (Murashige and Skoog, 1962) with 2% sucrose for 3–4 days under light (50 $\mu$Einsteins) at 23° C. Shoot apices (10–15 mm), including the shoot apical meristem, leaf primordia, and leaf bases, were isolated from germinated seedlings and cultured on meristem proliferation media (MPM) as previously reported in oat (Zhang et al. 1996). The MPM used in this instance was MS basal medium (M-5519, Sigma, St. Louis, Mo., USA) supplemented with 500 mg/L casein enzymatic hydrolysate (Sigma, St. Louis, Mo., USA), 3% sucrose, 2,4-dichlorophenoxyacetic acid (2,4-D) at levels of 0.3 or 0.5 mg/L, and 2.0 mg/L 6-benzylaminopurine (BAP).

For scanning electron-microscopy, in vitro cultured plant tissues from different stages were immersed in 20× volume of the fixing solution FAAT [47.4% v/v of 95% ethanol, 37.6% v/v of water, 10% v/v of formalin (37% formaldehyde), 5% v/v glacial acetic acid, 1% v/v Triton X-100] at 4° C. for 2 days, with gentle mixing on a rotary shaker. After 2 days, fixed plant materials were washed in 5–10× volume of 70% ethanol 3× and then dehydrated through an ethanol series (70%, 80%, 90%, 95%, 3×100%), 24 h in each solution. Dehydrated plant materials were critical point-dried in a Samdri-PTV-3B (Tousimis Research Corp., Rockville, Md., USA) with $CO_2$. Samples were mounted on aluminum stubs with colloidal silver paste (TED Pella Inc., Redding, Calif., USA), coated with 25 nm thickness of gold particles on a Polaron E5400 sputter coater and observed on a scanning electron microscope (Model ISIDS-130, ISI/TOPCON, NJ, USA).

Fixing and embedding of plant tissues followed essentially the protocol of Jackson (1991). For protein immunolocalization, the protocol described for KN1 in maize (Lucas et al. 1996) was followed. Briefly, tissue sections were dewaxed in Histoclear (National Diagnostics, Atlanta, Ga., USA) 2×, hydrated in a ethanol series (100, 100, 95, 85, 70, 50%) and PBS, permeabilized by treating with 0.1 mg/mL proteinase K (in PBS) for 15 min. After the treatment, slides were rinsed 3× in PBS and blocked for 30 min with 0.1% BSA/PBS for KN1 or 1% BSA/PBS for CDC2Zm.

For immunolocalization of KN1 or its cross-reactive protein(s), affinity-purified rabbit anti-KN 1 antiserum (1:10 dilution) (Smith et al. 1992) was used as the primary antibody, preimmune serum (1:10 dilution) was applied as a negative control. Plant tissues were incubated first with the anti-KN1 or preimmune antisera for 2 h at room temperature, rinsed with blocking agent 3×15 min, and incubated for 2 h with the second antibody [goat anti-rabbit alkaline phosphatase-conjugated antiserum (Boehringer Mannheim Corp., Indianapolis, Ind., USA) diluted 1:600 in 0.1% BSA/PBS], and then stained with the substrate 1-Step™ NBT/BCIP (Pierce, Rockford, Ill., USA), generating a dark blue precipitate. Plant tissues were counterstained with 0.05% fuchsin in 50% ethanol. For immunolocalization of CDC2Zm or its cross-reactive protein(s), rabbit CDC2Zm antiserum (1:200 dilution) was used as the primary antibody. Anti-CDC2Zm antiserum incubated for 2 h with the 17-amino acid CDC2Zm-specific peptide (Colasanti et al. 1993) at 1 mg/mL was applied to barley tissue as a negative control. Secondary antibody was the same as that for the KN1 experiment, however, a 1:200 dilution in 1% BSA/PBS was used.

Transgenic maize plants overexpressing KN1 were obtained by bombardment of an embryogenic callus line 44912 (Wan et al. 1995); the expression of KN1 in leaf tissues of $T_2$ plants was analyzed by immunolocalization experiments as described above. $T_3$ seeds were obtained by crossing $T_2$ transgenic maize plants with untransformed plants of maize cv. H99 or Pa91. Dried seeds of transgenic $T_3$, non-transgenic $T_3$ segregants, and untransformed maize cv. H99 were sterilized and germinated on MS basal medium. The expression of KN1 in the $T_3$ plants was confirmed by observing Kn1-like phenotypes in the leaves, e.g., vein clearing. At the 5–6 leaf stage, leaf tissue samples were cut into segments and cultured in vitro on MPM and callus-induction medium MS2,4-D (MS basal medium supplemented with 2.5 mg/L 2,4-D and 3% sucrose).

Results

Shoot apices of maize cv. H99 were isolated and cultured in vitro on MPM (seeds of cv. H99 were obtained from J. Widholm, University of Illinois). Shoot apical meristem in the shoot apex showed limited in vitro proliferation after two weeks. Axillary shoot meristems showed continuous in vitro proliferation after two weeks. After two to four more weeks in culture, multiple adventitious shoot meristems formed directly from the enlarged axillary shoot meristems. When the newly formed adventitious shoot meristems were transferred to MS hormone-free medium (Murashige and Skoog, 1962), they produced normal fertile plants; when the adventitious shoot meristems were maintained on MPM, they proliferated in a manner similar to the axillary shoot meristems and produced new adventitious shoot meristems. Descriptions of scanning electron-microscopic (SEM) analyses of adventitious shoot meristem formation from in vitro cultured shoot apices in other genotypes of maize have been shown in a previous report (Zhong et al., 1996). Stem elongation occurred during in vitro proliferation such that the shoot apical meristem and the proliferating axillary shoot meristems could not be captured in the same plane of focus.

Shoot apices of barley cv. Golden Promise were similarly cultured on MPM (seeds of cv. Golden Promise were obtained from P. Bregitzer and H. Bockelman at the National Small Grains and Potato Germplasm Research Facility, Aberdeen, Id.) After two weeks in culture, all vegetative shoot meristems exhibited enlarged smooth surfaces and proliferated to differing extents, with the shoot apical meristem being the smallest and the axillary shoot meristems being of greater size. The shoot apical meristem did not continue to proliferate, although the axillary shoot meristems did continue to proliferate. Four to six weeks after initiation, multiple adventitious shoot meristems had formed directly from the proliferation of axillary shoot meristems. The number of adventitious shoot meristems formed was dependent on the size of the enlarged meristematic domes with larger ones giving rise to greater numbers of adventitious shoot meristems. When the adventitious shoot meristems were transferred to MS hormone-free medium, they produced multiple normal shoots. When maintained on MPM medium, adventitious shoot meristems enlarged in exactly the same manner as the axillary shoot meristems.

Immunolocalization of CDC2Zm was conducted during in vitro shoot meristem proliferation in maize (anti-cdc2Zm serum was provided by J. Colasanti, Cold Spring Harbor Laboratory). Within the two week-old cultured shoot apex, a few random CDC2Zm-expressing cells were observed in the slightly enlarged shoot apical meristem and relatively more in leaf primordia. This pattern is similar to that observed in an uncultured shoot apex. In the initial proliferating axillary shoot meristems (pAXMs), a small number of CDC2Zm-expressing cells were similarly observed. Upon closer examination of the CDC2Zm-expressing cells, it was observed that the presence of CDC2Zm expression was correlated with cell division. In the later-stage pAXMs, relatively more CDC2ZM-expressing cells were observed than in earlier-stage pAXMs. In the newly formed adventitious shoot meristems, the relative number of expressing cells was similar to that observed in the shoot apical meristem.

Before being used to analyze barley meristems, the specificity of the maize CDC2Zm antiserum was tested in western blots. Protein extracts from barley in vitro leaf tissues and maize endosperm tissue (a maize endosperm protein sample was provided by W. Gruissem, UCB), a positive control, were analyzed in an immunoblot experiment using CDC2Zm antiserum. The predicted 34 kDa CDC2Zm band was detected in maize, and in barley a band of the same size as well as two additional protein bands of lower intensity were observed (data not shown). To show the specificity of the CDC2Zm antibody in immunolocalization, a 17 amino-acid CDC2Zm-specific peptide (Colasanti et al. 1993) was used to block binding of the CDC2Zm-specific antibody; in this case no immunostaining was observed, demonstrating the specificity of the maize CDC2Zm antiserum in barley tissues.

In the uncultured barley shoot apex, as in maize, a few random cells expressing protein(s) that cross-reacted with anti-CDC2Zm were localized in the shoot apical meristem and relatively more CDC2-expressing cells were observed in the third and fourth leaf primordia. In the initial in vitro pAXMs, a few cells containing protein(s) cross-reacting with anti-CDC2Zm were randomly distributed in the enlarged dome, similar to he shoot apical meristem. Relatively more CDC2-expressing cells were observed in the later-stage pAXMs, especially in the epidermal and subepidermal layers. In the newly formed adventitious shoot meristems, CDC2 expression in the meristematic dome resembled the pattern observed in the shoot apical meristem.

Expression of KN1 in maize was visualized during in vitro culture of shoot apical meristem and axillary shoot meristems and the formation of adventitious shoot meristems. Upon limited proliferation of the shoot apical meristem, expression of KN1 was observed in the dome, similar in some ways to that in an uncultured shoot apical meristem (Smith et al. 1992). All stages of the pAXMs were analyzed by immunolocalization of KN1; expression was uniformly maintained in all meristematic cells of the enlarged domes. In the multiple adventitious shoot meristems formed from the pAXMs, the expression pattern of KN1 was consistent with the possibility that adventitious shoot meristems form directly from KN 1-expressing cells, because the adventitious shoot meristems appeared to be directly connected to the KN1-expressing cells within the enlarged meristematic dome. The expression pattern of KN1 in adventitious shoot meristems was the same as in an uncultured shoot apical meristem (Smith et al. 1992).

In barley immunolocalization of KN1 cross-reacting protein(s) was conducted first on uncultured shoot apices and the results were compared to those using preimmune serum, with which no immunolocalization signal was observed. However, when using KN1 antiserum, a high-level of expression of KN1-homolog(s) was detected in the shoot apical meristem and ground meristematic tissue. No expression was detected in leaf founder cells ($P_0$) or differentiating leaves ($P_1$, $P_2$). The observed expression pattern of KN1-homolog(s) in the uncultured barley shoot apex resembled the pattern of KN1 seen in the uncultured maize shoot apex (Smith et al. 1992). In the initial pAXMs, the expression of KN1-homolog(s) was visualized in all actively proliferating meristematic cells; no expression was observed in the leaf (P1) tissues. In the later-stage pAXMs, expression of KN1-homolog(s) was similarly observed in enlarged meristematic domes (data not shown). The expression pattern in an adventitious shoot meristem was the same as that seen in the primary shoot apical meristem and multiple adventitious shoot meristems appeared to form directly from cells expressing the KN1-homolog(s).

Discussion

Multiple adventitious shoot meristems are induced directly from pAXMs in vitro. In classical microsurgery experiments, shoot meristems that were cut into small pieces, as small as 1/20th the size of the original meristem, first reformed an entire apical dome and then assumed the function of the shoot meristem (Snow and Snow 1951; Sussex 1952). In terms of the manipulation of the shoot meristem, the work described here is technically different from the classical experiments; however, both sets of experiments demonstrate that shoot meristem cells are capable of transmitting their meristematic character to progeny cells from which new shoot meristems can form directly.

In maize and barley, axillary shoot meristems continuously proliferate in vitro and produce multiple adventitious shoot meristems; however, shoot apical meristem response is very limited under the same in vitro conditions and multiple adventitious shoot meristem formation is not induced.

Analysis of expression of CDC2Zm or its homolog(s) during in vitro axillary shoot meristem proliferation in maize and barley showed that expression of these proteins is roughly correlated with cell-proliferation in vitro. In the meristematic dome of an uncultured shoot apical meristem, a few randomly expressing cells were observed, consistent with earlier observations that the frequency of cell division is low in the shoot meristem compared to organ primordia, for example (Steeves and Sussex 1989). In the later stages of in vitro proliferation of axillary shoot meristems, CDC2 expression occurred in more cells that in the uncultured shoot apical meristem. These CDC2-expressing cells were localized mainly in the outer few layers of the proliferating axillary shoot meristem in barley. These results suggest that the in vitro-cultured axillary shoot meristems are triggered to undergo continuous cell division and likely form multiple adventitious shoot meristems.

Immunolocalization using KN1 antiserum in the barley shoot apex were the same as those using KN1 antiserum in maize. Thus, expression of the KN1-homolog(s) in barley is an accurate molecular marker for shoot meristem formation and may be used to supplement or verify visual identification of meristematic tissues. When the expression patterns of maize KN1 or barley KN1-homolog(s) were analyzed during continuous in vitro proliferation of axillary shoot meristems, expression of KN1 or KN1-homolog(s) was retained in the enlarged meristematic domes and multiple adventitious shoot meristems appeared to form directly from the KN1-expressing cells.

Example 2

Transformation of Barley cv. Harrington Using Shoot Meristematic Cultures

Prior attempts to transform the barley variety Harrington and other commercial cultivars using published protocols have been largely unsuccessful—no stably transformed lines were identified from which green plants could be regenerated. The efficacy of the transformation protocol described here was tested in the barley variety Harrington, which is the current quality standard for two-rowed malting barley and is widely grown in North America. Harrington cannot be transformed using published transformation methods.

Materials and Methods

Dry seeds of four cultivars of barley, two two-rowed varieties, Harrington (HT) and Crystal (CR), one variety of six-rowed, Morex (MR), and one dihaploid (DH 10) derived from a cross of Morex and Steptoe, were germinated aseptically on MS medium (Murashige and Skoog 1962) to produce sterile seedlings. Seeds of the barley cvs. Crystal, Morex, and DH10 were provided by P. Bregitzer, USDA-ARS, Arbedeen, ID; and cv. Harrington was obtained from B. Rossnagel, University of Saskatchewan, Saskatoon, Canada.

The shoot apices were isolated from the germinated seedlings of barley cultivars, HT, CR, MR, and DH10, and cultured on the shoot meristem proliferation medium MPM, comprising: MS+2.0 mg/L BAP+0.5 mg/L 2,4-D+500 mg/L casein hydrolysate+30 g/L sucrose, pH 5.6–5.8 (Zhang et al. 1996), or on MPM-MC which was MPM in which 30 g/L maltose replaced the sucrose and the level of $CuSO_4$ in (0.1 $\mu$M) was increased fifty-fold to 5.0 $\mu$M.

Shoot meristematic cultures (SMCs) of barley cv. HT were cut and placed in the petri dishes containing MPM-MC. Two transformation experiments were conducted (Table 1): 1) co-transformation with pAHC20 and pAHC15 (Christensen and Quail 1996) using the particle inflow gun as previously described (Koprek et al., 1996); 2) pUbi1NPTII-1 and pAHC15, using the Bio-Rad PDS1000He device as described (Lemaux et al. 1996). Osmoticum treatment was applied in both experiments. Bombarded SMCs were grown on MPM-MC for the first 2–3 weeks. After that, transformed tissues were selected on MPM-MC containing 3–5 mg/L of bialaphos for bar and 40–50 mg/L of G418 for nptII. After 3–4 months on selection, putative transgenic tissues were obtained and transferred to MS plus 2.0 mg/L BAP to induce vegetative shoot development. Putative bar-transformed shoots were transferred to MS containing 3–5 mg/L bialaphos to induce root development. Putative nptII-transformed shoots were rooted on MS medium without adding G418. Putative transgenic plants were transferred to the greenhouse. Progeny from transgenic barley plants were also individually harvested.

DNA samples were isolated from leaf tissue of greenhouse-grown plants using a urea extraction method (Cone 1989), digested with Hind III and/or EcoR I for plants transformed with pAHC20, pAHC15, or pUBiINPTII-1, transferred to Zeta-Probe GT blotting membrane (Bio-Rad Laboratories, CA 94547) using downward alkaline blotting (Koetsier et al. 1993) and hybridized with 0.6 kb fragment of bar and 1.8 kb of uidA using manufacture's instructions (Instruction Manual, Zeta-Probe GT Blotting Membranes). After washing, the blot was exposed to Kodak BioMax MS film (Fisher Scientific, IL).

Mature $T_1$ and $T_2$ seeds were harvested, surface-sterlized, and germinated on MS basal medium. Portions of young roots from each germinated seedlings were tested for GUS expression by histochemical staining with x-gluc (Jefferson et al. 1987). Germinated seedlings were then transferred to MS medium with either 3–5 mg/L bialaphos to test for PAT (phosphinothricin acetyltransferase, product of bar), or 40–50 mg/L G418 for NPTII. An additional test for expression of herbicide resistance in greenhouse-grown plants involved leaf painting with 1% Basta solution (Hoechest AG, Frankfurt, Germany); plants were scored seven days after herbicide application. Chi-square analysis was applied to the segregation ratios for transgene expression in progeny. For analysis of physical transmission of bar and uidA, genomic DNA samples isolated from progeny plants were examined by PCR.

Results

Using the culturing medium MPM (i.e., without copper or maltose), the frequency of SMC induction from the four barley cultivars was very low, 10–20% from HT and CR, 0–10% from MR and DH10; none of them produced long-term SMCs on MPM. Modification of copper and maltose concentrations in the MPM was undertaken to improve the response of the shoot apices from the four barley cultivars. In previous experimentation on the in vitro culturing of barley microspores and immature embryos, maltose (Finnie et al. 1989) and $CuSO_4$ (Dahleen 1996) were separately found to improve the in vitro response of these types of tissues. These two components were tested individually and combined in MPM to observe their effects on in vitro proliferation of meristematic tissues from the four cultivars. Maltose alone reduced the production of brown tissue that had negative effects on the in vitro cultures. The addition of a high level of $CuSO_4$ (5 $\mu$M) alone, when any proliferation occured, only promoted shoot development from the SMCs. The combination of maltose and high level $CuSO_4$ however dramatically improved the frequenency of proliferation from the four barley cultivars, to 80–90% for HT, 50–70% for CR and DH10, and 30–40% for MR. After continuously selecting for the faster-proliferating SMCs during subculture on MPM-MC, long-term SMCs from all of the barley cultivars except MR were established.

From the three barley cultivars which produced long-term SMCs, HT was chosen for transformation experiments because of its commercial importance. Nine-month-old SMCs of HT were used as the target tissue in two transformation experiments (Table 1). Sets of three petri dishes of HT SMCs were bombarded with either pAHC20 and pAHC15, or pUbiNPTII-1 and pAHC15. After 3–4 month on selection media, two putative transformants, one from each experiment, were identified by their fast-growing characteristics on the selection media. Greater than 20 putative $T_0$ plants were produced from the bialaphos-resistant line, eight from the G418-resistant line. DNA hybridization analysis of multiple $T_0$ plants from each putative transgenic line confirmed the stable integrations of bar/nptII and uidA, with integration copies ranging from 2 to 6 as indicated from the lanes digested with a unique cut of Hind III. Expression of GUS was observed in the nptII-transformed line, but not in the bar-line. The bar-containing barley line had high fertility (60–70% seed set); the other line containing nptII had inviable pollen, and mature seeds were produced only after out-crossing with wild-type pollen. Segregation of transgene expression was analyzed in the $T_1$ and $T_2$ progeny of the two transgenic barley lines. Five $T_0$ plants from the bar-containing line were analyzed for expression of herbicide resistance in $T_1$ progeny, all of them exhibited a 3:1 segregation ratio (Table 2). Fourteen $T_1$ plants were analyzed for segregation of herbicide resistance in their $T_2$ progeny, five were homozygotes that produced 100% resistant $T_2$ progeny, the other nine were hemizygotes with 3:1 segregation. From the transgenic line transformed with nptII and uidA, expression of NPTII and GUS was observed in out-crossed $T_1$ progeny; however, the limited number of mature seeds precluded statistical analysis of segregation ratios.

Discussion

These results demonstrate the successful transformation of commercial barley cv. Harrington using shoot meristematic cultures (SMCs) derived from germinated seedlings, and a specialy formulated meristem proliferation medium. Using SMCs as the transformation target tissue provides several advantages. Not only can this approch be extended to other commercial varieties, but germinated seedlings for initial explants can be taken from dry seeds, obviating the need for growth of donor plants under tightly controlled environmental conditions to provide immature embryos (for example, as described by Wan and Lemaux 1994).

Transgenic SMCs of barley are high regenerable: the improvement in regenerability using SMCs is probably due to differences in the in vitro proliferation process of SMCs. During this process, shoot meristematic cells do not go through a callus phase or a de-differentiation process. Rather, they remain in a shoot meristamtic cell state from which vegetative shoots can be directly induced.

TABLE 1

Transformation of oat and barley using in vitro SMCs and $T_0$ plant analysis

| Plasmids used | Bombardment (Petri dishes[1]) | Transgenic Lines | $T_0$-Plants | Transgene Expression PAT | GUS | Fertility (%) |
|---|---|---|---|---|---|---|
| a. Oat cv. Garry | | | | | | |
| 1) pDM802 | 5 | OTs-1 | 12 | + | + | 0[2] |
| | | OTs-2, 3, 4 | 27 | + | + | 10–60 |
| | | OTs-5 | 8 | + | + | 60–70 |
| 2) pAHC20 + pAHC15 | 3 | OTm-2 | 3 | + | + | 70–80 |

TABLE 1-continued

Transformation of oat and barley
using in vitro SMCs and T₀ plant analysis

| Plasmids used | Bombardment (Petri dishes[1]) | Transgenic Lines | T₀ - Plants | Transgene Expression PAT | Transgene Expression GUS | Fertility (%) |
|---|---|---|---|---|---|---|
| | | OTm-3 | 4 | + | + | 0[2] |
| | | OTm-4 | 4 | + | − | 20–30 |
| | | OTm-5 | 3 | + | − | 10–20 |
| b. Barley cv. Harrington | | | | | | |
| 1) pAHC20 + pAHC15 | 3 | BTm-1 | 26 | + | − | 60–80 |
| 2) pUbiNPTII-1 + pAHC15 | 3 | BTt-1 | 6 | + (NPTII) | + | 0[2] |

[1]Each petri dish contained ca. 40 3 × 4 mm pieces excised from SMCs.
[2]Progeny produced only when outcrossing with non-transgenic pollen.

TABLE 2

Segregation of transgene expression in $T_1$ and $T_2$ progeny of oat and barley

| Transgenic plants (T₀) | T1 GUS (+/−) | T1 PAT (+/−) | | T2 PAT (+/−) |
|---|---|---|---|---|
| a) Oat cv. Garry | | | | |
| 1) OTs-2,3,4 | | | | |
| OTs-2(3)[1] | 15/49 | 48/16* | OTs-2(3)-1 | 50/14* |
| OTs-2(5) | 24/72 | 65/20* | OTs-2(3)-2 | 55/16* |
| OTs-3(1) | 4/14 | n.d.[2] | OTs-3(7)-1 | 12/22 |
| OTs-3(7) | 16/20 | 20/16 | OTs-3(7)-3 | 10/26 |
| OTs-3(5) | 6/46 | 8/44 | OTs-3(7)-4 | 8/31 |
| OTs-4(7) | 5/9 | n.d. | | |
| OTs-4(6) | 4/12 | 6/10 | | |
| OTs-4(2) | 19/58 | 31/45 | OTs-4(2)-1 | 19/31 |
| | | | OTs-4(2)-2 | 18/24 |
| 2) OTs-5 | | | | |
| OTs-5(1) | 52/42 | 78/24* | OTs-5(1)-5 | 47/19* |
| | | | OTs-5(2)-1 | 25/20 |
| OTs-5(2) | n.d. | 24/19 | OTs-5(2)-2 | 26/22 |
| | | | OTs-5(2)-3 | 25/17 |
| | | | OTs-5(2)-4 | 19/26 |
| 3) OTm-2 | | | | |
| OTm-2(1) | n.d. | 68/31* | | |
| OTm-2(2) | 35/25 | 52/20* | OTm-2(2)-1 | 38/21* |
| | | | OTm-2(2)-2 | 46/20* |
| OTm-2(3) | n.d. | 25/23 | OTm-2(3)-3 | 21/13 |
| 4) OTm-4 | | | | |
| OTm-4(1) | n.e.[3] | 31/22 | | |
| OTm-4(2) | n.e. | 41/42 | OTm-4(2)-2 | 42/49 |
| | | | OTm-4(2)-1 | 29/21 |
| b) Barley cv. Harrington | | | | |
| 1) BTt-1 | | | | |
| BTt-1(1) | n.e. | 22/4* | | |
| BTt-1(2) | n.e. | 15/5* | 9 T1 plants | 3:1* |
| | | | 5 T1 plants | 1:0* |
| BTt-1(3) | n.e. | 36/10* | | |
| BTt-1(4) | n.e. | 27/8* | | |
| BTt-1(5) | n.e. | 31/9* | | |

[1]Line designation, e. g. OTs-2(5) = Transgenic line OTs-line 2 and the 5th sibling plant.
[2]n.d. = not determined.
[3]n.e. = no expression.
*Fit 3:1 or 1:0 ratio based on Chi-square analysis with a 0.05 limit of probablity and one degree of freedom;
$T_2$ progeny were derived from individual $T_1$ hemizygous plant.

Example 3

Transformation of Oat cv. Garry Using Shoot Meristematic Cultures with bar and uidA Materials and Methods Seeds of oat cv. Garry were provided by Harold Bockelman, USDA-ARS Small Grains Germplasm Center, Aberdeen, Id. Dry seeds from oat cv. Garry were germinated aseptically on MS medium (Murashige and Skoog 1962) to produce sterile seedlings.

Vegetative shoot apices (1.0–1.5 cm) were cut from 7-day old germinated seedlings by cutting out the roots and the upper part of leaves, cultured on the shoot meristem proliferation medium (MPM): MS+2.0 mg/L BAP+0.5 mg/L 2,4-D+500 mg/L casein hydrolysate+30 g/L sucrose, pH 5.6–5.8. Induced SMCs were subcultured on MPM every two weeks.

Six-month-old SMCs of oat were cut (3–5 mm pieces) and placed with the proliferating sides up in the center of 10 cm-diamenter petri dish containing MPM. Two transformation experiments were carried out (Table 1): 1) pDM803, bombardment using the Bio-Rad PDS1000He device with 1100 psi and 1 μg DNA/0.3 mg 1.0 μm gold particle per bombardment, without osmoticum treatment; 2) co-transformation with pAHC20 and pAHC15 (Christensen and Quail 1996) at 1:1 molar ratio, bombardment using the same device with the parameters as previously described (Lemaux et al. 1996), with osmoticum treatment (0.2 M mannitol and 0.2 M sorbitol, four hours before and sixteen hours after bombardment). For both experiments, bombarded SMCs were grown on MPM for the first 2–3 weeks. After that, selection was carried out on MPM containing 2 mg/L of bialaphos (Meiji Seika Kaisha, Ltd., Japan). After 3–4 months on selection, herbicide-resistant and fast-growing SMCs were transferred to MS plus 2.0 mg/L BAP to induce vegetative shoot development. Putative bar-transformed shoots were transferred to MS containing 3–5 mg/L bialaphos to induce root development. Putative transgenic plants at 4–5 leaf stage were transferred to Supersoil (R. McClellan, S. San Francisco, Calif.) and grown in the greenhouse. Progeny from transgenic plants were individually harvested.

DNA samples were isolated from leaf tissue of greenhouse-grown plants using a urea extraction method (Cone 1989), digested with Cla I and EcoR I for plants transformed with pDM803, or Hind III and EcoR I for plants transformed with pAHC20 and pAHC15, transferred to Zeta-Probe GT blotting membrane (Bio-Rad Laboratories, CA 94547) using downward alkaline blotting (Koetsier et al. 1993) and hybridized with 0.6 kb fragment of bar and 1.8 kb of uidA using manufacture's instructions (Instruction Manual, Zeta-Probe GT Blotting Membranes). After washing, the blot was exposed to Kodak BioMax MS film (Fisher Scientific, IL).

Mature $T_1$ and $T_2$ seeds were harvested, surface-sterlized, and germinated on MS basal medium. Portions of young roots from each germinated seedlings were tested for GUS expression by histochemical staining with x-gluc (Jefferson et al. 1987). Germinated seedlings were then transferred to MS medium with either 3–5 mg/L bialaphos to test for PAT (phosphinothricin acetyltransferase, product of bar ), or 40–50 mg/L G418 for NPTII. An additional test for expression of herbicide resistance in greenhouse-grown plants involved leaf painting with 1% Basta solution (Hoechest A G, Frankfurt, Germany); plants were scored seven days after herbicide application. Chi-square analysis was applied to the segregation ratios for transgene expression in progeny. For analysis of physical transmission of bar and uidA, genomic DNA samples isolated from progeny plants were examined by PCR.

Results

After 6–8 weeks on MPM, more than 90% of shoot apices of oat cv. Garry produced shoot meristematic cultures (SMCs). The induced SMCs continuously proliferated on MPM for extended times. Six-month-old SMCs of oat cv. Garry were used as initial targets in two transformation experiments (Table 1). In the experiment using pDM802, five petri dishes of tissues were bombarded. In the second experiment using pAHC20 and pAHC15, three petri dishes were bombarded. After 3–4 months of selection on 2 mg/L bialaphos, five resistant lines were obtained from the first experiment, four from the second experiment. Numerous $T_0$ plants from each putative transgenic line were regenerated, transferred to the greenhouse, and tested for transgene expression. The five putative transgenic lines transformed with pDM803 expressed PAT and GUS as evidenced by resistance of the leaves to herbicide application and GUS expression in roots and young leaf tissues (data not shown). Of the four putative transgenic lines co-transformed with pAHC20 and pAHC15, two of them expressed PAT only and two expressed both PAT and GUS. DNA samples from leaf tissues of $T_0$ plants were used in DNA hybridization analysis, the results of which showed that the five putative lines transformed with pDM803 were from three independent transgenic lines; the four lines co-transformed with pAHC20 and pAHC15 were all independent. The copy number of the transgenes varied from 3–10. Various levels of fertility of $T_0$ plants were observed among the seven oat transgenic lines, even among multiple $T_0$ plants from the same event (Table 1).

Segregation of transgene expression was analyzed in $T_1$ and $T_2$ progeny of the five fertile transgenic oat lines (OTs-2,3,4; OTs-5; OTm-2; OTm-4) (Table 2). Ten $T_0$ plants from the three GUS-expressing lines were examined for segregation of GUS expression in $T_1$ progeny, all of them segregated in less than the expected 3:1 ratio. Thirteen $T_0$ plants from the four PAT-expressing lines were examined for segregation of PAT expression in their $T_1$ progeny; at least one $T_0$ plant from each line (except OTm-4) had the expected 3:1 ratio.

PAT was expressed in more $T_1$ progeny than GUS, and there were variations in the segregation ratios of bar and uidA expression among the multiple $T_0$ plants analyzed from each transgenic line. For example, from the line of OTs-2, 3,4, two out of six $T_0$ plants tested had the 3:1 segregation ratio. Seventeen $T_1$ plants derived from eight $T_0$ plants (at least one $T_0$ plant from each transgenic line) were analyzed for segregation of herbicide resistance in their $T_2$ progeny: the $T_2$ generation segregation patterns were generally the same as those in the $T_1$ generation.

Since some of the transgenic $T_0$ and $T_1$ oat plants did not segregate in the expected ratios (3:1 from a hemizygote or 1:0 from a homozygote) for transgene expression, transmission of the transgenes was analyzed in $T_1$ and $T_2$ segregating progeny by PCR amplification of the bar and uidA transgenes (Table 3). The PCR analysis showed that the transgenic $T_0$ plant OTm-2(2) transmitted the transgenes in a expected 3:1 ratio. In this plant, the expression of PAT in $T_1$ progeny was consistent with the presence of bar as evidenced by the resistance to 5 mg/L bialaphos in MS medium. However, four out of 27 uidA-positive $T_1$ progeny did not express GUS. The other three plants appeared to transmit at less than the expected ratios (3:1 or 1:0). Similar to that in OTm-2(2), all of the bar-positive plants expressed PAT; however, two out of 11 uidA-positive plants from OTs-3 (7)-1 did not express GUS.

TABLE 3

| Transgenic plants | bar[1] (+/−) | PAT[2] (+/−) | uidA[1] (+/−) | GUS[3] (+/−) |
|---|---|---|---|---|
| $T_0$ plants | | | | |
| OTs-3(3) | 10/17 | 10/17 | n.d.[4] | n.d. |
| OTm-2(2) | 27/9 | 27/9 | 27/9 | 23/13 |
| $T_1$ plants | | | | |
| OTs-3(7)-1 | 11/18 | 11/18 | 11/18 | 9/20 |
| OTm-4(2)-2 | 42/49 | 42/49 | n.e. | n.e. |

[1]The presence of bar and uidA was analyzed by PCR.
[2]Germinated seedlings resistant to 5 mg/L bialaphos in MS medium was counted as PAT-positive (+).
[3]Germinated seedling roots stained with X-glu showing blue colour was counted as GUS-positive (+).
[4]n.d. not determined.
[5]n.e. no expression.

Discussion

The commercial oat cv. Garry was successfully transformed using shoot meristematic cultures (SMCs) derived from germinated seedlings as the transformation target tissue. As with the barley transformation protocol discussed above, the use of SMCs as target tissue provides some significant advantages over other transformation methods.

Transgenic SMCs of oat had a high regenerability—every selected transformed tissue produced regenerated plants. In contrast, previous transformation reports using embryos, regenerability of transgenic embryogenic callus was 36–57% in oat (Somers et al. 1992; Torbert et al. 1995).

Example 4
Transformation of Oat cv. Garry with Three Selectable Markers Using Shoot Meristem Tissues Plant Material and Culture of Explants Shoot meristematic cultures were induced from shoot apices of germinating of mature seeds of oat (*Avena saliva* L. cv. Garry) and proliferated as described above.

Plasmids

Plasmids, pAHC20, pAct1IHPT-4, pUbiINPTII-1 and pAct1IsGFP-1, were used for transformation. pAHC20 (Christensen and Quail 1996) contains bar driven by the maize ubiquitin promoter/first intron and terminated by the nos 3'-end. pAct1IHPT-4 contains the hygromycin phosphotransferase (hpt) coding sequence under control of the rice actin1 promoter (Act1), its intron and the nos 3' terminator. pUbiINPTII-1 contains the nptII gene driven by the maize ubiquitin promoter/first intron and terminated by nos. pAct1IsGFP-1 contains synthetic gfp gene (sgfp) (Chiu et al., 1996) controlled by the rice actin1 promoter and its intron and terminated by nos.

Particle Bombardment and Stable Transformation

Approximately four-month-old shoot meristem cultures were used for bombardment. The meristem tissues (3 to 4 mm in size) were transferred for osmotic pretreatment to meristem proliferation medium (MPM) containing equimolar amounts of mannitol and sorbitol to give a final concentration of 0.4 M. Four hours with osmoticum treatment, tissues were bombarded as previously described (Wan and Lemaux 1994; Lemaux et al. 1996). Gold particles (1.0 μm) were coated with 25 μg of an equimolar ratio of a mixture of pAct1IsGFP-1 and one of three plasmids, pAHC20, pAct1IHPT-4 and pUbiINPTII-1, followed by bombardment using a PDS-1000 He biolistic device (Bio-Rad, Inc., Hercules, Calif.) at 900 psi. Sixteen to 18 hr after bombardment, the bombarded tissues were placed on MPM without osmoticum and grown at 24±1° C. under dim light. Following the initial 10- to 14-day culturing period, each tissue was broken into 1 to 3 pieces depending on tissue size and selected with bialaphos (2 mg/L), hygromycin B (20 mg/L), or geneticin (G418; 30 to 50 mg/L). From the second round selection, tissues were subcultured at 3- to 4-week intervals and maintained on the same medium containing each selective agent. When sufficient quantities of tissue were available, they were moved to FHG regeneration medium (Hunter, 1988) with 2 mg/L bialaphos for bar or without selective agents for hpt and nptII. After four weeks on FHG medium, the regenerated shoots were transferred to Magenta boxes containing the rooting medium (MS medium without phytohormones). When the shoots reached the top of the box, plantlets were transferred to the soil.

Herbicide Application

To determine herbicide sensitivity of $T_0$ plants and their progeny, a section of leaf blade at the 4- to 5-leaf stage was painted using a cotton swab with a 0.25% solution (v/v) of Basta™ solution (starting concentration, 200 g/L phophinothricin, Hoechst A G, Frankfurt, Germany) plus 0.1% Tween 20. Plants were scored 1 week after herbicide application.

GFP Expression Detection by Fluorescence Microscopy

GFP expression was monitored at high magnification using a Zeiss Axiophot fluorescent microscope equipped with a Chroma filter block containing a 450–490 excitation filter and a LP520 emission barrier filter.

Genomic DNA Isolation, Polymerase Chain Reaction (PCR) and DNA Blot Hybridization To test for the presence of sgf, bar, hpt and nptII in genomic DNA of putatively transformed lines, 500 ng of genomic DNA was used for amplification by PCR using primer pairs specific for each gene. Amplifications were performed in a 25-μl reaction with Taq DNA polymerase (Promega, Madison, Wis.).

DNA Blot Hybridization Analysis

For DNA hybridization analysis, 10 μg of total genomic DNA from leaf tissue of each line was digested with either SacI or EcoRI, separated on a 1.0% agarose gel, transferred to Zeta-Probe GT membrane (Bio-Rad, Hercules, Calif.) and hybridized with a radiolabeled sgfp-specific probe following the manufacturer's instructions. The sgfp-containing 0.72-kb NcoI- NotI fragment from pAct1IsGFP-1 was purified by QIAEX gel extraction kit (QIAGEN, Chatsworth, Calif.) and labeled with a-$^{32}$P-dCTP using random primers.

Results

Bombardment and Selection for Transgenic Clones

Shoot meristem tissues were initiated and maintained on MPM for 4 to 5 months under dim light conditions. For bombardment about 30 to 40 pieces of tissues (3 to 4 mm in size) were placed on the same medium with 4-hr pre-osmoticum treatment. Sixteen to 18 hours after bombardment, the tissues were transferred to MPM without osmoticum and cultured for 10 to 14 days without selection. The first round of selection (second transfer) was on MPM supplemented with 2 mg/L bialphos for bar, 20 mg/L hygromycin B for hpt and 30–50 mg/L G418 for nptII selection; selection pressure was maintained at the same level for subsequent rounds. In general, selective agent-resistant tissues were observed at the third to fourth round selection. Transgenic tissues were regenerated on FHG regeneration medium and the plantlets transferred to soil and grown to maturity approximately 3 to 4 weeks after growth in rooting medium of the Magenta boxes.

Analysis of $T_0$ and $T_1$ Plants

After 8- to 16-week selection periods with each selective agent, 13 independent transgenic lines were obtained from 202 pieces of tissues, giving a 6.4% transformation frequency (Table 4). All 13 transformed lines were regenerable; 7 out of 12 lines tested (58%) were fertile. Strong GFP expression was detected in the meristem and other tissues of the transgenic lines. Expression of GFP in leaves and other green tissues was obscured by chlorophyll fluorescence.

Stable integration of the introduced genes in $T_0$ plants was confirmed by polymerase chain reaction (PCR) amplification and DNA hybridization analysis. All 13 transgenic lines produced the PCR-amplified-fragments for the appropriate selective markers and 8 lines had sgfp fragments, giving a 62% cotransformation frequency. However, coexpression frequency was only 25% (3/12).

Stable integration of the introduced sgfp gene in the transgenic oat lines was further confirmed by DNA hybridization analysis. Genomic DNA from 4 lines, transformed with pAct1IsGFP-1 and positive by PCR, were analyzed by DNA hybridization. Three lines (GRBarGfp-2, 4 and GRNptGfp-7), positive by GFP expression assay, contained the expected 1.98-kb and 1.54-kb fragments after digestion with SacI or EcoRI, respectively. Multiple copies of sgfp were integrated but only 1–2 copies had the expected size.

TABLE 4

Summary of transformation experiments for oat.

| Plasmids for bombardment | No. of explants bombarded | Transgenic oat lines | DNA PCR (T₀ leaf) gfp | bar | hpt | npt | Basta painting | GFP activity | GFP activity in T₁ seeds (+:−) | fertility | ETF** |
|---|---|---|---|---|---|---|---|---|---|---|---|
| pAHC20 | 60 | GRBarGfp-1 | + | + | | | − | − | 0:24 | fertile | 8.3% |
| + pAct1IGFP-1 | | GRBarGfp-2 | + | + | | | + | + | n.d. | sterile | |
| (bar, gfp) | | GRBarGfp-4 | + | + | | | + | + | n.d. | sterile | |
| | | GRBarGfp-5 | + | + | | | + | − | 0:34 | fertile | |
| | | GRBarGfp-6 | + | + | | | + | − | n.d. | sterile | |
| pAct1IHPT-4 | 64 | GRHptGfp-11 | − | | + | | | − | 0:30 | fertile | 3.1% |
| + pAct1IGFP-1 | | GRHptGfp-12 | − | | + | | | | 0:11 | fertile | |
| (hpt, gfp) | | GRHptGfp-13ᵃ | − | | − | | | | 0:25 | fertile | |
| pUbiINPTI1-1 | 78 | GRNptGfp-3 | − | | | + | | − | n.d. | fertile | 7.7% |
| + pAct1IGFP-1 | | GRNptGfp-6 | + | | | + | | − | 0:15 | fertile | |
| (nptII, gfp) | | GRNptGfp-7 | + | | | + | | + | 4:8 | fertile | |
| | | GRNptGfp-11 | − | | | + | | − | n.d. | sterile | |
| | | GRNptGfp-13 | + | | | + | | n.d.* | n.d. | sterile | |
| | | GRNptGfp-16 | − | | | + | | − | n.d. | n.d. | |
| Total | 202 | 13 lines | | | | | | | | 58% (7/12) | 6.4% |

*n.d.; not determined
**ETF; efficient transformation frequency = # regenerable lines/# independent transgenic lines
ᵃGRHptGfp-13 is an escape Example 5
Transformation of Wheat Commercial Varieties Using Shoot Meristematic Cultures Induced from Shoot Apex of Germinated Seedlings Dry seeds of wheat varieties Anza and Yecora Rojo were surface-sterlized and germinated on MS basal medium to produce germinating seedlings. Shoot apices isolated from the germinated seedlings were cultured on MPM or MPM-MC as described in Example 2 for barley. After 8–12 weeks on MPM, no shoot meristematic cultures had been maintained from the two genotypes. However, on the medium of MPM-MC, 30–40% of shoot apices of Anza and 50–60% of Yecora Rojo produced SMCs.

Regenerative meristematic tissue produced from wheat was then transformed using the protocol described for barley in Example 2.

Example 6
Genomic DNA Methylation Patterns of Barley Plants Derived from Shoot Meristematic Cells are more Stable than those from Embryogenic Callus Cells Under in vitro Stress The dynamic character of the plant genome may allow plants to adjust to environmental stress. In vitro culture is an ideal example of such environmental stress, resulting in genomic modification or instability. Changes in genomic DNA methylation patterns may be the initial step in genetic instability induced by in vitro culture. Before genetic mutation occurs, significant changes in genomic DNA methylation patterns can be observed in maize plants regenerated from in vitro embryogenic callus cells derived from the scutellum of immature embryos.

The genome of a given plant species or variety is relatively stable from generation to generation. During the sporophytic phase of development, vegetative shoot meristematic cells produce all of the initial cells needed to form other plant structures, such as the leaf, axillary shoot, inflorescence and floral meristems. Therefore, the integrity of the genome in these meristematic cells must be stably maintained during normal vegetative growth under stressful conditions.

Under the stress of in vitro culturing, genomic DNA methylation patterns in barley plants derived from shoot meristematic cells were more stable than plants derived from embryogenic callus cells. Shoot meristematic cells may have mechanisms to maintain the genome in a more stable state under stressful conditions. Genomic instability may occur primarily during the callus phase during or after in vitro de-differentiation.

Materials and Methods

For the starting material for in vitro culture, three single plant-derived (SPD) seeds from each of the barley varieties Golden Promise and Morex were germinated and grown under controlled conditions (Wan and Lemaux 1994) in growth chambers.

For the standard embryogenic callus induction (SECI) method (Wan and Lemaux 1994), a total of 30 immature embryos of Golden Promise and Morex were isolated at random from the three plants on three different days and cultured on MSC (MS+2.5 mg/L 2,4-D) medium, on which the embryogenic callus was also maintained during the three-month culture period. Callus induced from each immature embryo was maintained as an individual line and plants were regenerated on FHG medium (Hunter, 1988, and described in Kasha et al., 1990; the composition of FHG medium is 165 mg/L $NH_4NO_3$, 1.90 g/L $KNO_3$, 440 mg/L $CaCl_2.2H_2O$, 370 mg/L $MgSO_4.7H_2O$, 170 mg/L $KH_2PO_4$, 16.9 mg/L $MnSO_4.H_2O$, 8.6 mg/L $ZnSO_4.7H_2O$, 6.2 mg/L $H_3BO_3$, 0.83 mg/L KI, 0.25 mg/L $Na_2MoO_4.2H_2O$, 25 µg/L $CuSO_4.5H_2O$, 25 µg/L $CoCl_2.6H_2O$, 0.4 mg/L thiamine-HCl, 100 mg/L inositol, 730 mg/L glutamine, 62 g/L maltose, 27.8 mg/L $FeSO_4.7H_2O$, 33.5 mg/L $Na_2EDTA$, 1.0 mg/L BAP, 3 g/L Phytagel, pH 5.6) at one and three months.

In the modified embryogenic callus induction (MECI) method, another 20–30 randomly selected immature embryos were similarly isolated from both Golden Promise and Morex and cultured for one month on DBC1 medium (MS+2.5 mg/L 2,4-D+0.01 mg/L BAP+50×$CuSO_4$), followed by transfer to DBC2 medium (MS+2.5 mg/L 2,4-D+ 0.1 mg/L BAP+50×$CuSO_4$) for the second and third months. Plants were regenerated from these cultures at one and three months by transferring selected callus to FHG medium.

For the shoot meristem culture (SMC) method, 20 mature embryos were isolated randomly from the three Golden Promise plants and germinated on MS medium to produce in vitro seedlings; shoot apices were isolated and cultured on MPM medium (MS with 0.5 mg/L 2,4-D, 2.0 mg/L, BA, 500 mg/L casein hydrolsate and 30 g/L sucrose) for axillary shoot meristem proliferation (Zhang et al. 1996). Shoot apices isolated from the seedlings of Morex were cultured on MPM-MC (MS+0.5 mg/L 2,4-D+2.0 mg/L BAP+50× $CuSO_4$+30 g/L maltose), one or two plants from each shoot apex of Golden Promise and Morex were obtained from the three- and six-month old adventitious shoot meristem cultures. Seeds from the three original donor plants were collected, pooled and saved for later germination in the greenhouse as control plants. Regenerated plants ($R_0$) were transferred to the greenhouse and grown with control plants to produce $R_1$ seeds.

Leaf tissue was harvested at the 7–8 leaf stage from each $R_0$ plant and DNA isolated. DNA samples (10 $\mu$g) were digested with three methylation-sensitive enzymes (HpaII, MspI, HhaI) and the DNA separated by electrophoresis through a 0.8% agarose-TBE gel. DNA was transferred to a nylon membrane and DNA hybridization analysis was performed on the membrane using radioactively labeled probes. The six DNA probes used, ABG 010, ABG 498, ABG 602, ABC 155, ABC 256, Hor 1&2, were kindly provided by Dr. David Hoffman, USDA-ARS, Aberdeen, Id. Genomic DNA samples from $R_1$ plants were similarly collected and analyzed.

Results

In order to investigate the genomic DNA methylation pattern stability in plants from in vitro cultures initiated and maintained on the various culture protocols, genomic DNA from the seed-derived plants as control was isolated and analyzed for methylation pattern variation using six barley DNA probes, including three genomic (ABG498, ABG602, ABG010) and three cDNA probes (ABC256, ABC 155, Hor 1&2), and three methylation-sensitive enzymes (Hpa II, MspI, and Hha). The relative frequency of methylation pattern changes was quantitated by two methods. In the first method, any individual plant in which a band pattern change occured (addition, deletion, shift) was scored as a single variant. In the second method, each individual band change within a plant (addition, deletion, shift) was scored as a variant.

In the eight control Golden Promise plants analyzed using HpaII and the six DNA probes, there were differences in the degree of methylation pattern changes observed using the six probes. The methylation state as detected by the six probes was relatively stable among the control plants, except for one band change in one plant using ABG498. However, a greater degree of variability was observed using the probe Hor 1&2, with 2–3 band pattern changes detected among the eight control plants. Therefore, in analyzing results obtained with the probe Hor 1 &2, only changes in the number of bands detected were counted. Because of the variability seen with the Hor 1&2 probe in the control plants, only the remaining five probes were used in the comparative analysis of the plants derived from the three in vitro culture methods.

Using the SECI method, which produced embryogenic callus cells (Wan and Lemaux 1994) one month after initiation, 26 callus lines were obtained from the initial 30 immature embryos of Golden Promise, and ten lines from 30 immature embryos of Morex. Portions of the callus from each line of Golden Promise were transferred to FHG medium for plant regeneration. One or two plants from each line were regenerated and transferred to the greenhouse. Portions of the callus from ten Morex lines were transferred to DBC2 medium before being transferred to FHG for plant regeneration. An intermediate culturing step on DBC2 medium was necessary because it was not possible to regenerate plants from Morex callus by transferring the callus directly to FHG medium as in the SECI method (Wan and Lemaux 1994). Even with the use of an intermediate culturing step, only two one-month-old callus lines of Morex produced $R_0$ plants. The low regeneration frequency of Morex also resulted from the limited amount of callus that was induced from each immature embryo after one month in culture. From three-month old cultures, nineteen callus lines of Golden Promise produced $R_0$ plants. Similarly one or two plants from each line were regenerated and transferred to the greenhouse. Because of the greater amounts of callus that had been induced, four lines produced $R_0$ plants from three month-old Morex callus cultures using the same protocol as for one month-old cultures, and one to two plants were regenerated from each line.

Based on the results of the five DNA probes with HpaII and calculating variation on a per-plant basis, the average relative frequencies (ARFs) of variation in plants derived from the one-month old cultures from SECI (SECI-1) was 32.7%. In plants derived from the three-month old cultures of SECI (SECI-3), the ARFs increased to 64.0%. The frequency of variation detected varied when different probes were used, the three genomic DNA probes showing a relative higher variation in both SECI-1 and SECI-3 than with the two cDNA probes.

Both hypo- and hyper-methylation changes were observed, depending largely on which DNA probe was used. For example, probe ABG010 detected both hypo- and hyper-methylation changes; probe ABG498 detected primarily hypo-methylation changes; and probe ABG602 detected primarily hyper-methylation changes. Often, multiple plants derived from the same embryos displayed the same trends toward hypo- or hyper-methylation (for example, plants-1 and -2 of the SECI-3–29 line). In other cases, different trends toward methylation change were observed in multiple plants derived from the same embryo (for example, plants-1 and -2 of SECI-3–14 displayed hyper-methylation with the probe ABG010 versus hypo-methylation with probe ABG498). No correlations in trends of methylation pattern changes were observed in plants derived from the same embryo between one- and three-month old SECI cultures.

When using the methylation-sensitive enzyme MspI, no changes in methylation patterns were observed in any plants derived from SECI-1 or -3. For example, with probe ABG498 (which was found to be the most variable when analyzing HpaII-restricted DNA samples), the uniform pattern observed in the control plants was identical to that observed in DNA from plants derived from SECI-3 when digested with MspI, suggesting that DNA sequence changes did not occur. When genomic DNA samples from control plants were digested with HhaI and probed with the probes ABG498 and ABG010, no variation was observed. However, methylation pattern changes were detected in every plant derived from SECI-1 and -3.

For the SMC method, shoot apices from the germinated seedlings of twenty mature embryos of Golden Promise were cultured for axillary shoot meristem proliferation (Zhang et al. 1996). Shoot apices of Morex were cultured on a modified medium containing 50-fold higher levels of $CuSO_4$ and maltose (instead of surose) as the carbon source, since Morex did not proliferate on the medium for Golden Promise. Because of the relatively slow in vitro proliferation of shoot meristematic domes compared to callus, time points of three months (SMC-3) and six months (SMC-6) were chosen for regeneration of Golden Promise. From each line, one or two plants were regenerated from the SMC-3 and -6 both in Golden Promise and Morex, because of the higher plant regeneration ability (almost 100%), even in Morex.

The ARF in the plants from three-month-old SMC cultures (SMC-3) was much lower (4%) than in plants from SECI-1 cultures. Only one probe (ABG498) showed 20% of variants and the other four probes did not show any variation. The ARF of plants derived from six month-old cultures (SMC-6) increased to 24.0% but was markedly lower than for plants derived from SECI-3 (64.0%). As in SECI, the levels of variation were different among the five probes; the genomic DNA probes detected a relatively higher frequency of variations, particularly probe ABG498 (increased up to 80% of variants). There was little difference in the frequency of variants between SECI-3 and SMC-6 when calculated on a per-plant basis, but differences were clear if counted on a per-band basis (160% verus 90%). This discrepancy resulted because there was only one band change in each individual plant in SMC-6, but 2–3 bands changed in SECI-3.

To better understand why plants derived from shoot meristematic cells have relatively more stable methylation patterns than plants derived from embryogenic callus cells, we used the "MECI method." For the first month, immature embryos of Golden Promise and of Morex were isolated and cultured on DBC1 medium, on which embryogenic callus was induced from the immature scutellum as in SECI. After one month (MECI-1), portions of embryogenic callus from each line were transferred to regeneration medium for plant regeneration. On the regeneration medium, thirty-one embryogenic callus lines of Golden Promise produced $R_0$ plants and seven lines of Morex.

The remaining embryogenic callus tissue from each line was transferred to DBC2 medium [MS medium supplemented with 30 g/L maltose, 1.0 mg/L thiamine-HC1, 0.25 g/L myo-inositol, 1.0 g/L casein hydrolysate, 0.69 g/L proline, 2.5 mg/L 2,4-D, 0.1 mg/L BAP, 5.0 $\mu$M cupric sulfate, and solidified with 3.5 g/L Phytagel (Sigma, St. Louis, Mo.)] and continuously subcultured under dim light on DCB2 medium for the second and third months. During subculturing there was an apparent gradual shift from embryogenic callus growth to shoot meristematic growth, since more and more green sectors and leaf tissues developed. To verify this shift, tissues from MECI cultures maintained on DBC2 were sectioned and the expression pattern of KN1-homolog(s) was determined using immunolocalization with antibody to maize KN1, the expression of which we have determined to be a reliable molecular marker for in vitro shoot meristem formation in barley (see Example 1). Analysis of KN1-homolog expression in sections of MECI-cultured tissue demonstrated that the meristematic portion of the somatic embryo proliferated and produced multiple shoot meristems instead of a single shoot meristem. After two months of culture on DCB2, thirteen lines of Golden Promise and eight lines of Morex produced $R_0$ plants, and one or two plants were produced from each line.

Methylation in plants from MECI-1 was 31.1% per plant, similar to SECI-1 (32.7%). The frequency of variants from MECI-3 was 33.3%, which was similar to MECI-1 but much lower than SECI-3 (64.0%). These results showed that the genomic DNA methylation pattern stabilized after the cultures were transferred to DCB2 medium.

Based on the data using the five probes and calculating variation on a per plant basis, the average relative frequencies (ARFs) of variation of the one-month old cultures between SECI and MECI were similar (32.7% versus 31.1% per plant, respectively). In contrast, the ARF for the plants from the three-month-old SMC cultures was significantly lower (4%). For plants derived from later time points (three-month old cultures for SECI and MECI and six month-old cultures for SMC), the ARFs were increased for all three treatments. However, the increase for plants from the SECI method (64.0% per plant) was significantly greater than that from MECI (33.3%) or SMC (24.0%).

As noted above, the results of these analyses depended on the particular probe used and the trend among probes can be different from the data reflected in the ARF. For example, with probe ABG498, the relative frequencies in plants from the early and late time points of MECI were lower than in plants from comparable time points of SMC. In contrast, for the probe ABG602, the relative frequencies were higher for the plants from MECI than for those from SECI. The degree of genomic DNA methylation pattern variation clearly differs among plants deriving from different treatments and at different times.

More dramatic differences among the three treatments are observed when the results are analyzed on a per-band basis rather than a per-plant basis. The two calculations yield such different results because of data from the three genomic probes with which more than one band change is observed from an individual plant, particularly with plants derived from the SECI method. For example, with probe ABG498, the methylation pattern changes in plants derived from SECI-3 (160%) are clearly greater than from SMC-6 (90%). However, when compared on a per-plant basis, the difference between SECI-3 (100%) and SMC-6 (80%) was only 20%.

The analysis of methylation variation in Morex was hampered by the numbers of plants that could be regenerated from the SECI and MECI methods: two from SECI-1 and four from SECI-3, seven from MECI-1 and eight from MECI-3. This resulted from the very low regenerability of the callus, even using the improved protocol in which tissue was transferred to DBC2 before transfer to FHG. Therefore, a detailed comparative analysis could not be performed for Morex. However, limited analyses in the twelve plants derived from both SMC-1 and -3 showed a similarly low percentage of methylation pattern changes (16.7% and 41.5% with ABG 498 and 0% with ABG010), and the lack of regenerability likely reflected accumulation of methylation changes and mutations.

To test if the methylation pattern changes observed in $R_0$ plants of Golden Promise was inheritable, five $R_1$ plants deriving from each of the five $R_0$ plants (SECI-3-4-1, -3-10-1, -3-14-1, -3-16-1 and -3-29-1) of SECI-3, two (SMC-6–4 and -6-6) of SMC-6, and one (G6) of the controls, were analyzed by using HpaII and two probes, ABG498 and ABG010. The methylation analysis results showed the pattern in the five $R_1$ plants from the control (G6) was the same as that of the $R_0$ plant for both probes tested, demonstrating that the methylation patterns in these plants were stable from generation to generation. In $R_1$ plants from each of five $R_0$ plants of SECI-3, the patterns of methylation changes were inherited in their entirety from two $R_0$ plants (SECI-3-4-1 and SECI-3-14-1) as analyzed with both probes. The probing of SECI-3-14-1 with ABG010 indicated that the two $R_0$ plants were homozygous for the methylation changes. The patterns from the other three $R_0$ plants were also inherited. However, new bands were observed in a few of the five $R_1$ progeny plants. None of the five $R_1$ progeny of the $R_0$ plant SECI-3-29-1 showed the same pattern as either the $R_0$ plant or the control. In the five $R_1$ progeny of the two $R_0$ plants derived from SMC, the methylation patterns were 100% inherited when probed with ABG010. When probed with ABG498, SMC-6-4 was 100% inherited. However, in $R_1$ progeny derived from SMC-6-6, different patterns were observed in each of the five $R_1$ plants.

The correlation between the phenotypic performance (stature, time to flowering, etc.) of $R_1$ plants in the greenhouse with genomic DNA methylation pattern changes was determined. With respect to the two $R_0$ plants, the five $R_1$ plants from the $R_0$ plant GPM6-4, which did not show changes in their methylation patterns, had phenotypes that were similar to control $R_1$ plants. However, the five $R_1$ plants from the second $R_0$ plant that showed methylation pattern changes performed poorly (dwarfing, later flowering, etc.), similar to $R_1$ plants derived from the five $R_0$ plants, which showed different levels of methylation pattern changes derived from embryogenic callus.

Discussion

In these analyses, there were significant differences in the sensitivity with which probes detected methylation changes. Genomic probes appeared more sensitive than cDNA probes; for example ABG498 showed a range of variation on a per-plant basis of between 20–100%, ABG602 between 0–100%, and ABG010 between 0–86%; while ABC256 only ranged between 0–27% and ABC155 between 0–21%. In the SECI method, embryogenic callus cells were initiated from the immature scutellum and maintained as embryogenic callus on MSC medium. In MECI, embryogenic callus cells were similarly induced on DBC1 medium as in SECI for the first month. However, when embryogenic callus was transferred to DBC2 medium, the proliferation appeared to shift morphologically from embryogenic growth to shoot meristematic growth.

In the MECI treatment, the ARFs were lower than that in SECI but higher to the AFRs observed in SMC. The ARF from the MECI-3 cultures was very similar to that from the MECI-1 cultures and did not increase as much as that detected between the SECI-1 and SECI-3 cultures. This may result when MECI cultures were transferred to DBC2 medium, causing a shift trom embryogencsis to organogenesis. This is consistent with the observation that shoot meristematic cells in SMC were significantly more stable than embryogenic callus cells in SECI under in vitro stresses.

With MECI-derived plants, only probes ABG498 and 602 show a tendency toward increased variation with time, which can be explained by the presence of elevated copper levels in the media in MECI, since the different levels of 2,4-D and BAP present in SECI and SMC did not result in similar differences.

The difference in the results between the two calculations largely results from data from the three genomic probes with which more than one band change is observed from an individual plant, particularly with plants derived from the SECI method, further supporting the conclusion that genomic DNA methylation pattern changes in plants derived from SECI were even more severe.

Genomic DNA methylation patterns in plants derived from in vitro shoot meristematic cells were significantly more stable than those from the embryogenic cells in barley. The significant differences in genomic DNA methylation pattern changes can not be explained by differences preexisting in the different initial explants used (shoot meristematic dome versus immature scutellum). If the observed differences pre-existed as differences in stable epigenetic states between shoot meristematic cells and immature scutellum cells, the methylation pattern changes in plants derived from the one-month old embryogenic callus cells should be the same as that from the three-month old callus cells in SECI treatment and in vitro proliferation switching in MECI treatment should not be different from the SECI treatment in methylation pattern changes in plants derived from the three-month old cultures.

The different kinds and levels of hormones (2,4-D and BA) and elevated copper levels applied also cannot be fully responsible for the different levels of methylation pattern instability observed among the three treatments, since the ARFs of methylation changes between SECI-1 and MECI-1 were very similar (32.66% and 31.08%). When comparing MECI-1 (31.03%) to MECI-3 (33.32%), the methylation pattern changes did not increase as much as between SECI-1 (32.66%) and SECI-3 (64.00%), which suggests that increasing the BAP level to 0.1 mg/L stabilized the genomic methylation pattern. When comparing the results between SECI-1 (32.66%) and SMC-1 (4.0%), reducing the level of 2,4-D from 2.5 to 0.5 mg/L and adding BAP (2.0 mg/L) significantly stabilized the genomic methylation patterns.

Increasing the level of BAP and decreasing the level of 2,4-D appeared to be critical factors in the lower levels of methylation pattern changes observed in plants derived from SMC treatment. However, the effects of hormones on genomic DNA methylation changes during in vitro culture may in fact result from the effects of the different in vitro proliferation processes, shoot meristematic cells in SMC verus embryogenic callus cells in SECI. This conclusion is supported by the stabilization of genomic methylation patterns resulting when in vitro proliferation was switched from embryogenic callus cells in MECI-1 to shoot meristematic cells in MECI-3. The results, therefore, support the idea that cellular mechanisms control genome stability under various stress conditions, including in vitro culture. In in vitro proliferation of shoot meristematic cells, the controlling mechanisms are probably maintained, as reflected by the maintenance of expression of KN1 or KN1-homolog(s) (Zhang et al. 1996). These mechanisms are required for shoot meristematic cells to maintain the stability for a given species or variety under various stresses experienced during vegetative development. However, these cellular control mechanisms break down during in vitro dedifferentiation of plant cells to the callus state, including cells in the immature scutellum.

Epigenetic methylation changes in the plant genome are probably the first step in the genetic instability that results from in vitro culture. Our results show that shoot meristematic cells under in vitro stress have significantly more stable genomic methylation patterns, and thus greater genetic stability, that embryogenic callus cells in barley.

The results of our genomic methylation analysis in plants derived from the embryogenic callus cells induced from the immature scutellum in barley are consistent with the those observed in maize plants derived from the embryogenic callus that was likewise induced from immature scutellum (Kaeppler and Phillips 1993). Both experiments showed that genomic DNA methylation patterns were changed significantly in plants derived from the embryogenic callus. Methylation pattern changes were detected only when genomic DNA samples were digested with HpaII; no pattern change observed with MspI, indicating that sequence changes did not occur as frequently as the methylation modification in barley and maize (Kaeppler and Phillips 1993). Hypo-methylation was primarily observed in maize (Kaeppler and Phillips 1993). However, in barley, both hypo- and hyper-methylation changes were observed and were mainly dependent on the individual probes used. As in maize (Kaeppler and Phillips 1993), the changed methylation patterns in the individual plants were inherited by progeny plants, and both homo- and heterozygous states of methylation changes were observed. We also observed new methylation patterns in individual $R_1$ plants, which further supports previous observations that the epigenetic methylation of plant genome, once changed, cannot be stabilized through one generation and is usually maintained for several generations.

The differences observed among the three treatments were greater when analyzed on a per-band basis than on a per-plant basis, because of the multiple-band changes detected by certain DNA probes. Previous studies have indicated that there is probably a correlation in methylation changes between different sites within the same gene or the same region. Therefore, comparison analysis among different treatments on a per-plant basis is likely to be better than analysis on a per-band basis. Methylation pattern changes in the multiple regenerated plants derived from the same embryo can be the same or they can be different, and the likelihood that these patterns are different is higher when the culture period is prolonged. This result further indicates that the genomic methylation changes are induced during in vitro proliferation and do not exist in the initial explants.

Plant regenerability among the three in vitro culture methods was significantly different. Fertile plants can be easily obtained from the cultures from SMC and MECI-3, even from cultures that are more than one year old. However, no green, fertile plants can be regenerated from callus derived from the SECI treatment. In order to produce transgenic plants, shoot meristematic cells, with their relatively stable genome, are to be preferred as a transformation target in order to reduce somaclonal variation and instability of a transgene and its expression in transgenic plants. Alternatively, if embryogenic callus cells are used as a transformation target, the length of the callus phase should be reduced to a minimum, probably less than a month.

The effects of the different culturing methods on the fidelity and performance of the regenerated plants were studied in field trials. First-generation plants from the three culturing methods (SECI, MECI, and SMC) and the control plants were grown in the field in a split plot design at two locations. Agronomic data was collected on all plants and analyzed. With respect to plant height for Golden Promise plants, at the first regeneration date, SECI-plants were shorter than control; MECI and SMC plants were not significantly different than the control. At the second regeneration date, SECI and MECI-derived plants were shorter than the control; SMC-derived plants were not different from the control. Yield comparisons among methods for Golden Promise showed that SECI-and MECI-derived plants were equivalent; SMC-derived plants yielded better. In addition, for the first regeneration date, Golden Promise plants from MECI and SECI were more variable than the controls, but SMC plants were not different from the controls.

Example 7
Use of Meristem Cultures for Transformation Increases the Likelihood of Transgene Expression Stability Stable expression of transgenes is critical for efficient application of transformation technologies to plant breeding. Published transformation methods produce transgenic plants that vary in transgene expression not only between independent transformants but also among sibling plants that are progeny of the same transformed plant. Gene silencing mechanisms involved in this phenomenon may be associated with the position of the transgene in the plant genome, with methylation of the transgene, and also with genomic instability induced during in vitro culturing, for example.

With regard to methylation, the methylation pattern of transgenic barley plants can also be an important indicator of stable transgene expression. Cereal genomes, for example, contain large percentages of hypermethylated repeat DNA (80% in wheat/barley; 50% in rice), probably through non-random amplification of DNA segments. Treatment of chromosomal DNA with MluI or NruI, for example, restricts undermethylated sites, revealing a non-random distribution of sites within major repetitive blocks in the cereal genomes of barley, maize, wheat and rye (Moore 1995). The genome is believed to be formed from larger genomic structures of tens of kilobases which contain highly repeated, hypermethylated DNA interspersed with islands of undermethylated sequences, containing the genes. Certain elements in the barley genome, e.g. BIS 1 and Hi-10, have been shown to be amplifiable, prone to methylation (Moore et al. 1991) and localized to distinct restriction fragment size classes (Moore 1995). Recombination in large cereal genomes is predominantly confined to regions distal to the centromere (Moore 1995). Association of a transgene with such repeated DNA sequences could be determined using conventional Southern blotting of the DNA of a transgenic plant following restriction digestion with MluI or NruI, for example, and probing with transgene- and repeat-specific probes, or by using in situ hybridization techniques. Association of the transgene with such repeated DNA sequences is a negative indicator of stable, high-level transgene expression.

Various in vitro culture methods result in very different levels of methylation change. Stability of the transgene itself and its expression was studied in some of the transgenic lines obtained through the SECI method using Southern, PCR and in vitro biochemical assays to determine the presence and expression of transgenes. Few lines showed Mendelian inheritance of the transgene and its expression through four generations; most did not. In contrast, transgenic plants produced by the shoot meristem transformation protocol described here showed significantly more stable inheritance and expression patterns.

This invention provides methods for transforming monocot plants, particularly commercially important cereals including barley, wheat and oat, as well culture media that facilitate these transformation procedures. It will be apparent that the precise details of these methods and the described media may be varied or modified without departing from the spirit of the described invention. We claim all such modifications and variations that fall within the scope and spirit of the claims below.

References

Alberts et al. (1994) *Molecular Biology of the Cell,* 3rd edition, Garland Publishing Inc., New York, pp. 863–910.
Ausubel et al., eds. (1992, with periodic updates) *Current Protocols in Molecular Biology,* Greene Publishing and Wiley-Interscience, New York.
Bajaj (1989) *Biotechnology in Agriculture and Forestry* 8: *Plant Protoplasts and Genetic Engineering I,* Springer-Verlag, New York.
Barton and Poeting (1993) *Development* 119:823–831.
Becraft et al. (1996) *Science* 273:1406–1409.
Bregitzer et al. (1995) *Plant Cell Tiss. Org. Cult.* 43:229–235.
Christensen and Quail (1996) *Transgenic Res.* 5:1–6.
Chiu et al., (1996) *Curr Biol* 6: 325–330.
Chuck et al. (1996) *Plant Cell* 8:1277–1289.
Colasanti et al. (1991) *Proc. Natl. Acad. Sci. USA* 88:3377–3381.
Colasanti et al. (1993) *Plant Cell* 5:1101–1111.
Cone (1989) *Maize Genet Coop News Lett* 63: 68
Dahleen (1996). *Plant Cell Tiss Org Cult* 43: 267–269

Day and Ellis (1985) *Curr. Genet.* 9:671–678.
Devaux et al. (1993) *Mol. Gen. Genet.* 241:674–679.
Dunford and Walden (1991) *Curr. Genet.* 20:339–347.
Feiler and Jacobs (1 990) *Proc. Natl. Acad. Sci. USA* 87:5397–5401.
Ferreira et al. (1991) *Plant Cell* 3:531–540.
Finnie et al. (1989) *Plant Breed* 103: 110–118
Fobert et al (1994) *EMBO J.* 13:616–624.
Foroughi-Wehr et al. (1982) *Theor. Appl. Genet.* 62:233–239.
Freeling and Hake (1985) *Genetics* 111:617–634.
Fromm et al. (1986) *Nature* 319:791–793.
Gelinas et al. (1969) *Am. J Bot.* 56:671–678.
Gelvin et al. (1990) *Plant Molecular Biology Manual,* Kluwer Academic Publishers.
Goldenstein and Kronstadt (1986) *Theor. Appl. Genet.* 71:631–636.
Gordon-Kamm et al. (1990) *Plant Cell* 2:603.
Hake et al. (1989) *EMBO J.* 8:15–22.
Hang and Bregitzer (1993) *J. Hered.* 84:105–108
Hareven et al. (1996) *Cell* 84:735–744.
Hemerly et al. (1 993) *Plant Cell* 5:1711–1723.
Hirt et al. (1991) *Proc. Natl. Acad. Sci. USA* 88:1636–1640.
Hunter (1988) "Plant regeneration from microspores of barley, *Hordeum vulgare,*" PhD thesis, Wye College, University of London, Ashford, England.
Jackson (1991) "In-situ hybridisation in plants," In: Bowles et al., eds., *Molecular Plant Pathology: A Practical Approach,* Oxford University Press, pp. 163–166.
Jahne et al. (1991) *Plant Cell. Rep.* 10:1–6.
Jefferson et al.(1987) *EMBO J* 6: 3901–3907
Kaeppler and Phillips (1993) *In Vitro Cell Dev. Biol.* 29:125–130.
Kao et al. (1991) *Plant Cell Rep.* 9:595–601.
Kasha et al. (1990) "Haploids in cereal improvement: Anther and microspore culture," in: *Gene Manipulation in Plant Improvement II,* ed., Gustafson, Plenum, New York, pp. 213–235.
Koetsier et al.(1993) *Biotechniques* 15: 260–262
Koprek et al.(l996). *Plant Sci* 119: 79–91
Kott and Kasha (1984) *Can. J. Bot.* 62:1245–1249.
Larkin and Scowcroft (1981) *Theor. Appl. Genet.* 60:197–214.
Laux et al. (1996) *Development* 122:87–96.
Lehman et al. (1996) *Cell* 85:183–194.
Lemaux et al. (1996) *Bombardment-mediated transformation methods for barley,* Bio-Rad US/EG Bulletin 2007: 1–6.
Lewin (1994) *Genes V,* Oxford University Press: New York.
Lincoln et al. (1994) *Plant Cell* 6:1859–1876.
Long et al. (1996) *Nature* 379:66–69.
Lucas et al. (1996) *Science* 270:1980–1983.
Martinez et al. (1992) *Proc. Natl. Acad. Sci. USA* 89:7360–7364.
Matsuoka et al. (1993) *Plant Cell* 5:1039–1048.
Moore (1995) *Curr. Opinion Genet. & Dev.* 5:717–724.
Moore et al. (1991) *Genomics* 10:469–476.
Mouritzen and Holm (1994) *J. Plant Physiol.* 144:586–593.
Muller et al. (1995) *Nature* 374:727–730.
Murashige and Skoog (1962) *Physiol. Plant.* 15:473–497.
Pinkel et al., *Proc. Natl. Acad. Sci. USA* 85:9138–9142, 1988.
Potrykus et al. (1977) *Mol. Gen. Genet.* 156:347–350.
Pouwels et al. (1985, supp. 1987) *Cloning Vectors. A Laboratory Manual.*
Rieger et al. (1991) *Glossary of Genetics: Classical and Molecular,* 5th edition, Springer-Verlag: New York.
Salmenkallio-Marttila et al. (1995) *Plant Cell Rep.* 15:301–304.
Sambrook et al., eds. (1989) *Molecular Cloning: A Laboratory Manual,* 2nd ed., Cold Spring Harbor Laboratory Press: Cold Spring Harbor, N.Y.
Shaul et al. (1996) *Crit. Rev. Plant Sci.* 15:97–112.
Sinha et al. (1993) *Genes Dev.* 7:787–795.
Smith et al. (1992) *Development* 116:21–30.
Smith et al. (1995) *Dev. Genet.* 16:344–348.
Snow and Snow (1951) *Proc. R. Soc. Lond. Ser. B* 139:545–566.
Somers et al. (1992). *Bio/technology* 10: 1589–1594
Somers et al. (1994) Genetic engineering of oat. In: Henry R J (Ed.) Improvement of Cereal Quality by Genetic Engineering. Plenum Press, New York. pp 37–46
Souer et al. (1996) *Cell* 85:159–170.
Steeves and Sussex (1989) *Patterns in Plant Development,* 2nd edition, Cambridge University Press: Cambridge.
Sussex (1952)*Nature* 170:755–757.
Thorpe (1994) "Morphogenesis and regeneration," In: Vasil and Thorpe, eds., *Plant Cell and Tissue Culture,* Kluwer Academic Publishers, Dordrecht, pp. 17–36.
Torbert et al. (1995). *Plant Cell Rep* 14: 635–640
Vain et al. (1993) *Plant Cell Tissue and Organ Culture* 33:237–246.
van de Sande et al. (1996) *Science* 273:370–373.
Vasil and Vasil (1992) *Physiol. Plant.* 85:279–283, 1992.
Vollbrecht et al. (1981) *Nature* 350:241–243.
Wan and Lemaux (1994) *Plant Physiol.* 104:37–48.
Wan et al. (1 995) *Planta* 196:7–14.
Wan et al. (1994) *Plant Physiol* 104: 37–48
Weigel and Nilsson (1995) *Nature* 377:495–500.
Weissbach and Weissbach (1989) *Methods for Plant Molecular Biology,* Academic Press: New York.
Zhang et al. (1996) *J. Plant Physiol.* 148:667–671.
Zhang et al. (1 998) *Planta* 204: 542–549.
Zhong et al. (1996) *Plant Physiol.* 110: 1097–1107.
Ziauddin and Kasha (1990) *Euphytica* 48:279–286.

What is claimed is:

1. A method for transforming a plant comprising:

(a) culturing an isolated meristematic tissue of the plant on a meristem proliferation medium so as to produce adventitious meristematic cells in the isolated meristematic tissue;

(b) after step (a), introducing a nucleic acid into at least one of the adventitious meristematic cells, thereby producing a transformed cell comprising the nucleic acid;

(c) culturing the transformed cell on meristem proliferation medium so as to promote growth of transformed meristematic cells;

(d) selecting transformed meristematic cells or at least one structure thereof; and (e) regenerating a transformed plant from the transformed meristematic cells or structure thereof;

wherein the plant is a cereal plant, the nucleic acid is introduced into the adventitious meristematic cell by particle bombardment, the meristematic tissue is a shoot apex and the meristem proliferation medium comprises from 0 mg/L to about 3 mg/L of an auxin, from about 2 mg/L to about 8 mg/L of a cytokinin, from about 10 g/L to about 60 g/L of maltose or about 10 g/L to about 60 g/L of sucrose; and from about 0.1 μM to about 50 μM copper.

2. The method of claim 1 wherein the cereal plant is selected from the group consisting of: barley, oat, wheat, maize, sorghum, millet, rice, rye and triticale.

3. The method of claim 1 wherein the plant is a barley plant.

4. The method of claim 3, wherein the barley plant is selected from the group consisting of 'Harrington', 'Morex', 'Crystal', 'Stander', 'Moravian III', 'Galena', 'Salome', 'Steptoe', 'Klages' and 'Baronesse'.

5. The method of claim 1 wherein the plant is a wheat plant.

6. The methods of claim 5 wherein the wheat plant is selected from the group consisting of 'Anza', 'Karl', 'Bobwhite' and 'Yecora Rojo'.

7. The method of claim 1 wherein the plant is an oat plant.

* * * * *